United States Patent
Akimoto et al.

(10) Patent No.: US 9,360,564 B2
(45) Date of Patent: Jun. 7, 2016

(54) IMAGING DEVICE

(71) Applicant: SEMICONDUCTOR ENERGY LABORATORY CO., LTD., Atsugi-shi, Kanagawa-ken (JP)

(72) Inventors: Kengo Akimoto, Tochigi (JP); Junichi Koezuka, Tochigi (JP); Hironobu Takahashi, Tochigi (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 14/467,161

(22) Filed: Aug. 25, 2014

(65) Prior Publication Data

US 2015/0060675 A1    Mar. 5, 2015

(30) Foreign Application Priority Data

Aug. 30, 2013    (JP) .................................. 2013-179560

(51) Int. Cl.
| | |
|---|---|
| A61B 6/00 | (2006.01) |
| H01L 27/146 | (2006.01) |
| G01T 1/20 | (2006.01) |

(52) U.S. Cl.
CPC ........ *G01T 1/2018* (2013.01); *H01L 27/14663* (2013.01); *A61B 6/4208* (2013.01)

(58) Field of Classification Search
CPC ................ A61B 6/4208; G01T 1/2018; H01L 27/14663
See application file for complete search history.

(56) References Cited

U.S. PATENT DOCUMENTS

| | | | | |
|---|---|---|---|---|
| 4,734,588 A | * | 3/1988 | Akai ..................... | G01T 1/2018 250/366 |
| 5,248,885 A | * | 9/1993 | Sato ......................... | G01T 1/11 250/370.09 |
| 5,731,856 A | | 3/1998 | Kim et al. | |
| 5,744,864 A | | 4/1998 | Cillessen et al. | |
| 6,294,274 B1 | | 9/2001 | Kawazoe et al. | |
| 6,563,174 B2 | | 5/2003 | Kawasaki et al. | |
| 6,727,522 B1 | | 4/2004 | Kawasaki et al. | |

(Continued)

FOREIGN PATENT DOCUMENTS

| | | |
|---|---|---|
| EP | 1737044 A | 12/2006 |
| EP | 2226847 A | 9/2010 |

(Continued)

OTHER PUBLICATIONS

Coates.D et al., "Optical Studies of the Amorphous Liquid-Cholesteric Liquid Crystal Transition: The "Blue Phase"", Physics Letters, Sep. 10, 1973, vol. 45A, No. 2, pp. 115-116.

(Continued)

*Primary Examiner* — Mark R Gaworecki
(74) *Attorney, Agent, or Firm* — Nixon Peabody LLP; Jeffrey L. Costellia

(57) ABSTRACT

To provide an imaging device that is highly stable when exposed to radiation such as X-rays. The imaging device includes a substrate, a pixel circuit, and a scintillator which are stacked in order. The pixel circuit includes a light-receiving element and a circuit portion electrically connected to the light-receiving element. The substrate is provided with a heater. A transistor in the pixel circuit is heated by the passage of a current through the heater at times other than imaging, thus, degradation of the electrical characteristics of the transistor due to X-ray irradiation can be recovered.

25 Claims, 18 Drawing Sheets

(56) References Cited

U.S. PATENT DOCUMENTS

| | | | |
|---|---|---|---|
| 6,954,514 B2* | 10/2005 | Wischmann | G01T 1/2018 250/370.15 |
| 7,049,190 B2 | 5/2006 | Takeda et al. | |
| 7,061,014 B2 | 6/2006 | Hosono et al. | |
| 7,064,346 B2 | 6/2006 | Kawasaki et al. | |
| 7,105,868 B2 | 9/2006 | Nause et al. | |
| 7,211,825 B2 | 5/2007 | Shih et al. | |
| 7,282,782 B2 | 10/2007 | Hoffman et al. | |
| 7,297,977 B2 | 11/2007 | Hoffman et al. | |
| 7,323,356 B2 | 1/2008 | Hosono et al. | |
| 7,385,224 B2 | 6/2008 | Ishii et al. | |
| 7,402,506 B2 | 7/2008 | Levy et al. | |
| 7,411,209 B2 | 8/2008 | Endo et al. | |
| 7,453,065 B2 | 11/2008 | Saito et al. | |
| 7,453,087 B2 | 11/2008 | Iwasaki | |
| 7,462,862 B2 | 12/2008 | Hoffman et al. | |
| 7,468,304 B2 | 12/2008 | Kaji et al. | |
| 7,501,293 B2 | 3/2009 | Ito et al. | |
| 7,674,650 B2 | 3/2010 | Akimoto et al. | |
| 7,732,819 B2 | 6/2010 | Akimoto et al. | |
| 8,492,728 B2 | 7/2013 | Antonuk | |
| 2001/0046027 A1 | 11/2001 | Tai et al. | |
| 2002/0056838 A1 | 5/2002 | Ogawa | |
| 2002/0093581 A1 | 7/2002 | Ikeda et al. | |
| 2002/0132454 A1 | 9/2002 | Ohtsu et al. | |
| 2002/0159563 A1* | 10/2002 | Tashiro | G01T 1/2018 378/98.8 |
| 2003/0189401 A1 | 10/2003 | Kido et al. | |
| 2003/0218222 A1 | 11/2003 | Wager, III et al. | |
| 2004/0038446 A1 | 2/2004 | Takeda et al. | |
| 2004/0127038 A1 | 7/2004 | Carcia et al. | |
| 2005/0017302 A1 | 1/2005 | Hoffman | |
| 2005/0199959 A1 | 9/2005 | Chiang et al. | |
| 2006/0035452 A1 | 2/2006 | Carcia et al. | |
| 2006/0043377 A1 | 3/2006 | Hoffman et al. | |
| 2006/0091793 A1 | 5/2006 | Baude et al. | |
| 2006/0108529 A1 | 5/2006 | Saito et al. | |
| 2006/0108636 A1 | 5/2006 | Sano et al. | |
| 2006/0110867 A1 | 5/2006 | Yabuta et al. | |
| 2006/0113536 A1 | 6/2006 | Kumomi et al. | |
| 2006/0113539 A1 | 6/2006 | Sano et al. | |
| 2006/0113549 A1 | 6/2006 | Den et al. | |
| 2006/0113565 A1 | 6/2006 | Abe et al. | |
| 2006/0169973 A1 | 8/2006 | Isa et al. | |
| 2006/0170111 A1 | 8/2006 | Isa et al. | |
| 2006/0197092 A1 | 9/2006 | Hoffman et al. | |
| 2006/0208977 A1 | 9/2006 | Kimura | |
| 2006/0228974 A1 | 10/2006 | Thelss et al. | |
| 2006/0231882 A1 | 10/2006 | Kim et al. | |
| 2006/0237647 A1 | 10/2006 | Ikeda et al. | |
| 2006/0238135 A1 | 10/2006 | Kimura | |
| 2006/0244107 A1 | 11/2006 | Sugihara et al. | |
| 2006/0284171 A1 | 12/2006 | Levy et al. | |
| 2006/0284172 A1 | 12/2006 | Ishii | |
| 2006/0292777 A1 | 12/2006 | Dunbar | |
| 2007/0024187 A1 | 2/2007 | Shin et al. | |
| 2007/0046191 A1 | 3/2007 | Saito | |
| 2007/0052025 A1 | 3/2007 | Yabuta | |
| 2007/0054507 A1 | 3/2007 | Kaji et al. | |
| 2007/0090365 A1 | 4/2007 | Hayashi et al. | |
| 2007/0108446 A1 | 5/2007 | Akimoto | |
| 2007/0152217 A1 | 7/2007 | Lai et al. | |
| 2007/0172591 A1 | 7/2007 | Seo et al. | |
| 2007/0187678 A1 | 8/2007 | Hirao et al. | |
| 2007/0187760 A1 | 8/2007 | Furuta et al. | |
| 2007/0194379 A1 | 8/2007 | Hosono et al. | |
| 2007/0252928 A1 | 11/2007 | Ito et al. | |
| 2007/0272922 A1 | 11/2007 | Kim et al. | |
| 2007/0287296 A1 | 12/2007 | Chang | |
| 2008/0006877 A1 | 1/2008 | Mardilovich et al. | |
| 2008/0038882 A1 | 2/2008 | Takechi et al. | |
| 2008/0038929 A1 | 2/2008 | Chang | |
| 2008/0050595 A1 | 2/2008 | Nakagawara et al. | |
| 2008/0073653 A1 | 3/2008 | Iwasaki | |
| 2008/0083950 A1 | 4/2008 | Pan et al. | |
| 2008/0106191 A1 | 5/2008 | Kawase | |
| 2008/0128689 A1 | 6/2008 | Lee et al. | |
| 2008/0129195 A1 | 6/2008 | Ishizaki et al. | |
| 2008/0166834 A1 | 7/2008 | Kim et al. | |
| 2008/0182358 A1 | 7/2008 | Cowdery-Corvan et al. | |
| 2008/0224133 A1 | 9/2008 | Park et al. | |
| 2008/0254569 A1 | 10/2008 | Hoffman et al. | |
| 2008/0258139 A1 | 10/2008 | Ito et al. | |
| 2008/0258140 A1 | 10/2008 | Lee et al. | |
| 2008/0258141 A1 | 10/2008 | Park et al. | |
| 2008/0258143 A1 | 10/2008 | Kim et al. | |
| 2008/0296568 A1 | 12/2008 | Ryu et al. | |
| 2009/0068773 A1 | 3/2009 | Lai et al. | |
| 2009/0073325 A1 | 3/2009 | Kuwabara et al. | |
| 2009/0114910 A1 | 5/2009 | Chang | |
| 2009/0134399 A1 | 5/2009 | Sakakura et al. | |
| 2009/0152506 A1 | 6/2009 | Umeda et al. | |
| 2009/0152541 A1 | 6/2009 | Maekawa et al. | |
| 2009/0278122 A1 | 11/2009 | Hosono et al. | |
| 2009/0280600 A1 | 11/2009 | Hosono et al. | |
| 2010/0065844 A1 | 3/2010 | Tokunaga | |
| 2010/0092800 A1 | 4/2010 | Itagaki et al. | |
| 2010/0109002 A1 | 5/2010 | Itagaki et al. | |
| 2010/0182282 A1 | 7/2010 | Kurokawa et al. | |
| 2011/0176038 A1 | 7/2011 | Kurokawa et al. | |
| 2014/0054466 A1 | 2/2014 | Kurokawa et al. | |
| 2014/0056405 A1 | 2/2014 | Kurokawa et al. | |

FOREIGN PATENT DOCUMENTS

| | | | |
|---|---|---|---|
| JP | 60-198861 A | 10/1985 | |
| JP | 63-210022 A | 8/1988 | |
| JP | 63-210023 A | 8/1988 | |
| JP | 63-210024 A | 8/1988 | |
| JP | 63-215519 A | 9/1988 | |
| JP | 63-239117 A | 10/1988 | |
| JP | 63-265818 A | 11/1988 | |
| JP | 02-164067 A | 6/1990 | |
| JP | 05-251705 A | 9/1993 | |
| JP | 08-264794 A | 10/1996 | |
| JP | 11-505377 | 5/1999 | |
| JP | 2000-044236 A | 2/2000 | |
| JP | 2000-150900 A | 5/2000 | |
| JP | 2002-076356 A | 3/2002 | |
| JP | 2002-151669 A | 5/2002 | |
| JP | 2002-289859 A | 10/2002 | |
| JP | 2003-086000 A | 3/2003 | |
| JP | 2003-086808 A | 3/2003 | |
| JP | 2004-103957 A | 4/2004 | |
| JP | 2004-273614 A | 9/2004 | |
| JP | 2004-273732 A | 9/2004 | |
| WO | WO-2004/114391 | 12/2004 | |

OTHER PUBLICATIONS

Meiboom.S et al., "Theory of the Blue Phase of Cholesteric Liquid Crystals", Phys. Rev. Lett. (Physical Review Letters), May 4, 1981, vol. 46, No. 18, pp. 1216-1219.

Costello.M et al., "Electron Microscopy of a Cholesteric Liquid Crystal and Its Blue Phase", Phys. Rev. A (Physical Review. A), May 1, 1984, vol. 29, No. 5, pp. 2957-2959.

Kimizuka.N et al., "Spinel, YbFe2O4, and Yb2Fe3O7 Types of Structures for Compounds in the In2O3 and Sc2O3—A2O3—BO Systems [A; Fe, Ga, or Al; B: Mg, Mn, Fe, Ni, Cu,or Zn] at Temperatures Over 1000°C", Journal of Solid State Chemistry, 1985, vol. 60, pp. 382-384.

Nakamura.M et al., "The phase relations in the In2O3—Ga2ZnO4—ZnO system at 1350°C", Journal of Solid State Chemistry, Aug. 1, 1991, vol. 93, No. 2, pp. 298-315.

Kitzerow.H et al., "Observation of Blue Phases in Chiral Networks", Liquid Crystals, 1993, vol. 14, No. 3, pp. 911-916.

Kimizuka.N et al., "Syntheses and Single-Crystal Data of Homologous Compounds, In2O3(ZnO)m (m=3, 4, and 5), InGaO3(ZnO03, and Ga2O3(ZnO)m (m=7, 8, 9, and 16) in the In2O3—ZnGa2O4—ZnO System", Journal of Solid State Chemistry, Apr. 1, 1995, vol. 116, No. 1, pp. 170-178.

(56) References Cited

OTHER PUBLICATIONS

Chern.H et al., "An Analytical Model for the Above-Threshold Characteristics of Characteristics of Polysilicon Thin-Film Transistors", IEEE Transactions on Electron Devices, Jul. 1, 1995, vol. 42, No. 7, pp. 1240-1246.
Prins.M et al., "A Ferroelectric Transparent Thin-Film Transistor", Appl. Phys. Lett. (Applied Physics Letters), Jun. 17, 1996, vol. 68, No. 25, pp. 3650-3652.
Li.C et al., "Modulated Structures of Homologous Compounds InMO3(ZnO)m (M=In,Ga; m=Integer) Described by Four-Dimensional Superspace Group", Journal of Solid State Chemistry, 1998, vol. 139, pp. 347-355.
Kikuchi.H et al., "Polymer-Stabilized Liquid Crystal Blue Phases", Nature Materials, Sep. 2, 2002, vol. 1, pp. 64-68.
Tsuda.K et al., "Ultra Low Power Consumption Technologies for Mobile TFT-LCDs ", IDW '02 : Proceedings of the 9th International Display Workshops, Dec. 4, 2002, pp. 295-298.
Nomura.K et al., "Thin-Film Transistor Fabricated in Single-Crystalline Transparent Oxide Semiconductor", Science, May 23, 2003, vol. 300, No. 5623, pp. 1269-1272.
Ikeda.T et al., "Full-Functional System Liquid Crystal Display Using Cg-Silicon Technology", SID Digest '04 : SID International Symposium Digest of Technical Papers, 2004, vol. 35, pp. 860-863.
Nomura.K et al., "Room-Temperature Fabrication of Transparent Flexible Thin-Film Transistors Using Amorphous Oxide Semiconductors", Nature, Nov. 25, 2004, vol. 432, pp. 488-492.
Dembo.H et al., "RFCPUS on Glass and Plastic Substrates Fabricated by TFT Transfer Technology", IEDM 05: Technical Digest of International Electron Devices Meeting, Dec. 5, 2005, pp. 1067-1069.
Kanno.H et al., "White Stacked Electrophosphorecent Organic Light-Emitting Devices Employing MOO3 as a Charge-Generation Layer", Adv. Mater. (Advanced Materials), 2006, vol. 18, No. 3, pp. 339-342.
Lee.H et al., "Current Status of, Challenges to, and Perspective View of AM-OLED ", IDW '06 : Proceedings of the 13th International Display Workshops, Dec. 7, 2006, pp. 663-666.
Hosono.H, "68.3:Invited Paper:Transparent Amorphous Oxide Semiconductors for High Performance TFT", SID Digest '07 : SID International Symposium Digest of Technical Papers, 2007, vol. 38, pp. 1830-1833.
Hirao.T et al., "Novel Top-Gate Zinc Oxide Thin-Film Transistors (ZnO TFTs) for AMLCDs", J. Soc. Inf. Display (Journal of the Society for Information Display), 2007, vol. 15, No. 1, pp. 17-22.
Park.S et al., "Challenge to Future Displays: Transparent AM-OLED Driven by Peald Grown ZnO TFT", IMID '07 Digest, 2007, pp. 1249-1252.
Kikuchi.H et al., "62.2:Invited Paper:Fast Electro-Optical Switching in Polymer-Stabilized Liqiud Crystalline Blue Phases for Display Application", SID Digest '07 : SID International Symposium Digest of Technical Papers, 2007, vol. 38, pp. 1737-1740.
Miyasaka.M, "SUFTLA Flexible Microelectronics on Their Way to Business", SID Digest '07 : SID International Symposium Digest of Technical Papers, 2007, vol. 38, pp. 1673-1676.
Kurokawa.Y et al., "UHF RFCPUS on Flexible and Glass Substrates for Secure RFID Systems", Journal of Solid-State Circuits , 2008, vol. 43, No. 1, pp. 292-299.
Jeong.J et al., "3.1: Distinguished Paper: 12.1-Inch WXGA AMOLED Display Driven by Indium—Gallium—Zinc Oxide TFTs Array", SID Digest '08 : SID International Symposium Digest of Technical Papers, May 20, 2008, vol. 39, No. 1, pp. 1-4.
Lee.J et al., "World's Largest (15-Inch) XGA AMLCD Panel Using IGZO Oxide TFT", SID Digest '08 : SID International Symposium Digest of Technical Papers, May 20, 2008, vol. 39, pp. 625-628.
Park.J et al., "Amorphous Indium—Gallium—Zinc Oxide TFTs and Their Application for Large Size AMOLED", AM-FPD '08 Digest of Technical Papers, Jul. 2, 2008, pp. 275-278.
Takahashi.M et al., "Theoretical Analysis of IGZO Transparent Amorphous Oxide Semiconductor", IDW '08 : Proceedings of the 15th International Display Workshops, Dec. 3, 2008, pp. 1637-1640.

Sakata.J et al., "Development of 4.0-In. AMOLED Display With Driver Circuit Using Amorphous In—Ga—Zn—Oxide TFTs", IDW '09 : Proceedings of the 16th International Display Workshops, 2009, pp. 689-692.
Asaoka.Y et al., "29.1:Polarizer-Free Reflective LCD Combined With Ultra Low-Power Driving Technology", SID Digest '09 : SID International Symposium Digest of Technical Papers, May 31, 2009, pp. 395-398.
Nowatari.H et al., "60.2: Intermediate Connector With Suppressed Voltage Loss for White Tandem OLEDs", SID Digest '09 : SID International Symposium Digest of Technical Papers, May 31, 2009, vol. 40, pp. 899-902.
Jin.D et al., "65.2:Distinguished Paper:World-Largest (6.5") Flexible Full Color Top Emission AMOLED Display on Plastic Film and Its Bending Properties", SID Digest '09 : SID International Symposium Digest of Technical Papers, May 31, 2009, pp. 983-985.
Lee.M et al., "15.4:Excellent Performance of Indium—Oxide-Based Thin-Film Transistors by DC Sputtering", SID Digest '09 : SID International Symposium Digest of Technical Papers, May 31, 2009, pp. 191-193.
Cho.D et al., "21.2:Al and Sn-Doped Zinc Indium Oxide Thin Film Transistors for AMOLED Back-Plane", SID Digest '09 : SID International Symposium Digest of Technical Papers, May 31, 2009, pp. 280-283.
Kikuchi.H et al., "39.1:Invited Paper:Optically Isotropic Nano-Structured Liquid Crystal Composites for Display Applications", SID Digest '09 : SID International Symposium Digest of Technical Papers, May 31, 2009, pp. 578-581.
Osada.T et al., "15.2: Development of Driver-Integrated Panel using Amorphous In—Ga—Zn—Oxide TFT", SID Digest '09 : SID International Symposium Digest of Technical Papers, May 31, 2009, pp. 184-187.
Ohara.H et al., "21.3:4.0 In. QVGA AMOLED Display Using In—Ga—Zn—Oxide TFTs With a Novel Passivation Layer", SID Digest '09 : SID International Symposium Digest of Technical Papers, May 31, 2009, pp. 284-287.
Godo.H et al., "P-9:Numerical Analysis on Temperature Dependence of Characteristics of Amorphous In—Ga—Zn—Oxide TFT", SID Digest '09 : SID International Symposium Digest of Technical Papers, May 31, 2009, pp. 1110-1112.
Osada.T et al., "Development of Driver-Integrated Panel Using Amorphous In—Ga—Zn—Oxide TFT", AM-FPD '09 Digest of Technical Papers, Jul. 1, 2009, pp. 33-36.
Godo.H et al., "Temperature Dependence of Characteristics and Electronic Structure for Amorphous In—Ga—Zn—Oxide TFT", AM-FPD '09 Digest of Technical Papers, Jul. 1, 2009, pp. 41-44.
Ohara.H et al., "Amorphous In—Ga—Zn—Oxide TFTs with Suppressed Variation for 4.0 inch QVGA AMOLED Display", AM-FPD '09 Digest of Technical Papers, Jul. 1, 2009, pp. 227-230, The Japan Society of Applied Physics.
Park.J et al., "High performance amorphous oxide thin film transistors with self-aligned top-gate structure", IEDM 09: Technical Digest of International Electron Devices Meeting, Dec. 7, 2009, pp. 191-194.
Nakamura.M, "Synthesis of Homologous Compound with New Long-Period Structure", Nirim Newsletter, Mar. 1, 1995, vol. 150, pp. 1-4.
Hosono.H et al., "Working hypothesis to explore novel wide band gap electrically conducting amorphous oxides and examples", J. Non-Cryst. Solids (Journal of Non-Crystalline Solids), 1996, vol. 198-200, pp. 165-169.
Orita.M et al., "Mechanism of Electrical Conductivity of Transparent InGaZnO4", Phys. Rev. B (Physical Review. B), Jan. 15, 2000, vol. 61, No. 3, pp. 1811-1816.
Van de Walle.C, "Hydrogen as a Cause of Doping in Zinc Oxide", Phys. Rev. Lett. (Physical Review Letters), Jul. 31, 2000, vol. 85, No. 5, pp. 1012-1015.
Orita.M et al., "Amorphous transparent conductive oxide InGaO3(ZnO)m (m<4):a Zn4s conductor", Philosophical Magazine, 2001, vol. 81, No. 5, pp. 501-515.
Janotti.A et al., "Oxygen Vacancies in ZnO", Appl. Phys. Lett. (Applied Physics Letters), 2005, vol. 87, pp. 122102-1-122102-3.

(56) References Cited

OTHER PUBLICATIONS

Clark.S et al., "First Principles Methods Using Castep", Zeitschrift fur Kristallographie, 2005, vol. 220, pp. 567-570.
Nomura.K et al., "Amorphous Oxide Semiconductors for High-Performance Flexible Thin-Film Transistors", Jpn. J. Appl. Phys. (Japanese Journal of Applied Physics), 2006, vol. 45, No. 5B, pp. 4303-4308.
Janotti.A et al., "Native Point Defects in ZnO", Phys. Rev. B (Physical Review. B), Oct. 4, 2007, vol. 76, No. 16, pp. 165202-1-165202-22.
Lany.S et al., "Dopability, Intrinsic Conductivity, and Nonstoichiometry of Transparent Conducting Oxides", Phys. Rev. Lett. (Physical Review Letters), Jan. 26, 2007, vol. 98, pp. 045501-1-045501-4.
Park.J et al., "Improvements in the Device Characteristics of Amorphous Indium Gallium Zinc Oxide Thin-Film Transistors by Ar Plasma Treatment", Appl. Phys. Lett. (Applied Physics Letters), Jun. 26, 2007, vol. 90, No. 26, pp. 262106-1-262106-3.
Park.J et al., "Electronic Transport Properties of Amorphous Indium—Gallium—Zinc Oxide Semiconductor Upon Exposure to Water", Appl. Phys. Lett. (Applied Physics Letters), 2008, vol. 92, pp. 072104-1-072104-3.
Hsieh.H et al., "P-29:Modeling of Amorphous Oxide Semiconductor Thin Film Transistors and Subgap Density of States", SID Digest '08 : SID International Symposium Digest of Technical Papers, May 20, 2008, vol. 39, pp. 1277-1280.
Oba.F et al "Defect energetics in ZnO: A hybrid Hartree-Fock density functional study", Phys. Rev. B (Physical Review. B), 2008, vol. 77, pp. 245202-1-245202-6.
Kim.S et al., "High-Performance oxide thin film transistors passivated by various gas plasmas", 214th ECS Meeting, 2008, No. 2317, ECS.
Hayashi.R et al., "42.1: Invited Paper: Improved Amorphous In—Ga—Zn—O TFTs", SID Digest '08 : SID International Symposium Digest of Technical Papers, May 20, 2008, vol. 39, pp. 621-624.
Son.K et al., "42.4L: Late-News Paper: 4 Inch QVGA AMOLED Driven by the Threshold Voltage Controlled Amorphous GIZO (Ga2O3—In2O3—ZnO) TFT", SID Digest '08 : SID International Symposium Digest of Technical Papers, May 20, 2008, vol. 39, pp. 633-636.
Park.Sang-Hee et al., "42.3: Transparent ZnO Thin Film Transistor for the Application of High Aperture Ratio Bottom Emission AM-OLED Display", SID Digest '08 : SID International Symposium Digest of Technical Papers, May 20, 2008, vol. 39, pp. 629-632.
Fung.T et al., "2-D Numerical Simulation of High Performance Amorphous In—Ga—Zn—O TFTs for Flat Panel Displays", AM-FPD '08 Digest of Technical Papers, Jul. 2, 2008, pp. 251-252, The Japan Society of Applied Physics.
Mo.Y et al., "Amorphous Oxide TFT Backplanes for Large Size AMOLED Displays", IDW '08 : Proceedings of the 6th International Display Workshops, Dec. 3, 2008, pp. 581-584.
Asakuma.N et al., "Crystallization and Reduction of Sol-Gel-Derived Zinc Oxide Films by Irradiation With Ultraviolet Lamp", Journal of Sol-Gel Science and Technology, 2003, vol. 26, pp. 181-184.
Fortunato.E et al., "Wide-Bandgap High-Mobility ZnO Thin-Film Transistors Produced at Room Temperature", Appl. Phys. Lett. (Applied Physics Letters), Sep. 27, 2004, vol. 85, No. 13, pp. 2541-2543.
Masuda.S et al., "Transparent thin film transistors using ZnO as an active channel layer and their electrical properties", J. Appl. Phys. (Journal of Applied Physics), Feb. 1, 2003, vol. 93, No. 3, pp. 1624-1630.
Oh.M et al., "Improving the Gate Stability of ZnO Thin-Film Transistors With Aluminum Oxide Dielectric Layers", J. Electrochem. Soc. (Journal of the Electrochemical Society), 2008, vol. 155, No. 12, pp. H1009-H1014.
Park.J et al., "Dry etching of ZnO films and plasma-induced damage to optical properties", J. Vac. Sci. Technol. B (Journal of Vacuum Science & Technolgy B), Mar. 1, 2003, vol. 21, No. 2, pp. 800-803.
Ueno.K et al., "Field-Effect Transistor on SrTiO3 With Sputtered Al2O3 Gate Insulator", Appl. Phys. Lett. (Applied Physics Letters), Sep. 1, 2003, vol. 83, No. 9, pp. 1755-1757.
Nomura.K et al., "Carrier transport in transparent oxide semiconductor with intrinsic structural randomness probed using single-crystalline InGaO3(ZnO)5 films", Appl. Phys. Lett. (Applied Physics Letters), Sep. 13, 2004, vol. 85, No. 11, pp. 1993-1995.

\* cited by examiner

IMAGING DEVICE

BACKGROUND OF THE INVENTION

1. Field of the Invention

The present invention relates to an object, a method, or a manufacturing method. In addition, the present invention relates to a process, a machine, manufacture, or a composition of matter. In particular, the present invention relates to, for example, a semiconductor device, a display device, a light-emitting device, a power storage device, a photoelectric conversion device, an imaging device, a driving method thereof, or a manufacturing method thereof. More particularly, the present invention relates to an imaging device including a scintillator.

2. Description of the Related Art

In medical practice, a medical diagnostic imaging device using X-ray film photography has been in wide use.

Since the imaging method using X-ray films involves a complicated management of the X-ray films, digitization of images is in progress. A known method for digitizing images uses an imaging plate. An imaging plate emits light when being irradiated with X-rays and the light is sensed with a scanner, so that digitized images can be obtained.

The imaging plate is a plate coated with a material (a photostimulable phosphor) emitting light by X-ray irradiation (this property is referred to as photostimulability) and has higher detection sensitivity to X-ray absorption difference than an X-ray film does. The imaging plate can be re-used because data of X-ray irradiation on the plate can be erased. However, the data that the imaging plate acquires is analog data, which needs to be digitized in a later process.

For this reason, in recent years, attention has been focused on flat panel detectors capable of acquiring digital data directly (e.g., Patent Documents 1 and 2). Flat panel detectors have direct and indirect conversion systems. In the direct conversion system, X-rays are directly converted into electrical charges with the use of an X-ray detecting element. In the indirect conversion system, X-rays are converted into visible light with a scintillator and the light is converted into electrical charges by a photodiode. In either system, a flat panel detector includes a plurality of pixel circuits arranged in a matrix.

REFERENCE

Patent Document

[Patent Document 1] Japanese Published Patent Application No. H2-164067
[Patent Document 2] Japanese Published Patent Application No. 2002-151669

SUMMARY OF THE INVENTION

A transistor included in each pixel circuit of a flat panel detector includes a semiconductor material or an insulating material. When the semiconductor material or the insulating material is exposed to radiation such as X-rays having strong energy, defect states, fixed charges, and the like are generated in some cases, thereby varying the electrical characteristics of the transistor.

Such a phenomenon may occur with a slight amount of radiation that passes through a scintillator, leading to increased power consumption or reduced reliability of a flat panel detector.

In view of the above, an object of one embodiment of the present invention is to provide an imaging device that is highly stable when exposed to radiation such as X-rays. Another object of one embodiment of the present invention is to provide an imaging device with a high resolution. Another object of one embodiment of the present invention is to provide an imaging device capable of taking images with a low dose of radiation. Another object of one embodiment of the present invention is to provide an imaging device with a low power consumption. Another object of one embodiment of the present invention is to provide a highly reliable imaging device. Another object of one embodiment of the present invention is to provide an imaging device having a display function. Another object of one embodiment of the present invention is to provide a novel imaging device or the like.

Note that the descriptions of these objects do not disturb the existence of other objects. Note that in one embodiment of the present invention, there is no need to achieve all the objects. Note that other objects will be apparent from and can be derived from the description of the specification, the drawings, the claims, and the like.

One embodiment of the present invention relates to an imaging device that includes a pixel circuit provided with a transistor using an oxide semiconductor, and that takes an image with radiation such as X-rays.

One embodiment of the present invention is an imaging device including a substrate, a pixel circuit, and a scintillator which are stacked in order. The pixel circuit includes a light-receiving element and a circuit portion electrically connected to the light-receiving element. The substrate is provided with a heater.

One embodiment of the present invention is an imaging device including a light-emitting device, a substrate, a pixel circuit, and a scintillator which are stacked in order. The pixel circuit includes a light-receiving element and a circuit portion electrically connected to the light-receiving element. The substrate is provided with a heater. Light is emitted from the light-emitting device to the pixel circuit.

The light-emitting device preferably emits monochromatic light with a wavelength of 500 nm to 600 nm or a mixture of colors including light in this wavelength range.

The pixel circuit preferably includes a top-gate transistor using an oxide semiconductor for a channel formation region.

One embodiment of the present invention is an imaging device including a substrate, a pixel circuit, and a scintillator which are stacked in order. The pixel circuit includes a light-receiving element and an imaging circuit portion electrically connected to the light-receiving element, and a light-emitting element and a light-emitting circuit portion electrically connected to the light-emitting element. The substrate is provided with a heater.

In the imaging devices of the above three embodiments, the light-receiving element can be a photodiode or a variable resistor including a semiconductor layer between a pair of electrodes.

The substrate and the heater may have light-transmitting properties.

The light-emitting element preferably emits monochromatic light with a wavelength of 500 nm to 600 nm or a mixture of colors including light in this wavelength range.

In the imaging device including the light-emitting element, the pixel circuit preferably includes a bottom-gate transistor using an oxide semiconductor for a channel formation region.

Owing to one embodiment of the present invention, an imaging device that is highly stable when exposed to radiation such as X-rays can be provided. An imaging device with a high resolution can be provided. An imaging device capable of taking images with a low dose of radiation can be provided. An imaging device with a low power consumption can be provided. A highly reliable imaging device can be provided. An imaging device having a display function can be provided. A novel imaging device or the like can be provided. Note that one embodiment of the present invention is not limited to these effects. For example, depending on the circumstances or conditions, one embodiment of the present invention might produce another effect. Furthermore, depending on the circumstances or conditions, one embodiment of the present invention might not produce any of the above effects.

DETAILED DESCRIPTION OF THE INVENTION

Figure 1A:
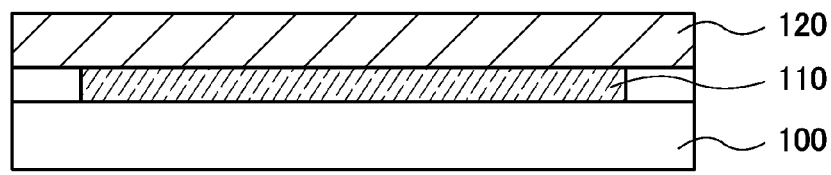
FIGS. 1A and 1B are cross-sectional views of imaging devices.

Embodiments will be described in detail with reference to drawings. Note that the present invention is not limited to the following description and it will be readily appreciated by those skilled in the art that modes and details can be modified in various ways without departing from the spirit and the scope of the present invention. Therefore, the present invention should not construed as being limited to the description of the embodiments below. Note that in the structures of the present invention described below, the same portions or portions having similar functions are denoted by the same reference numerals in different drawings, and the description thereof is not repeated in some cases. It is also to be noted that the same components are denoted by different hatching patterns in different drawings, or the hatching patterns are omitted in some cases.

For example, in this specification and the like, an explicit description "X and Y are connected" means that X and Y are electrically connected, X and Y are functionally connected, and X and Y are directly connected. Accordingly, without limiting to a predetermined connection relation, for example, a connection relation shown in drawings or texts, another connection relation is included in the drawings or the texts.

Here, X and Y each denote an object (e.g., a device, an element, a circuit, a wiring, an electrode, a terminal, a conductive film, or a layer).

For example, in the case where X and Y are directly connected, X and Y are connected without an element that enables electrical connection between X and Y (e.g., a switch, a transistor, a capacitor, an inductor, a resistor, a diode, a display element, a light-emitting element, or a load) interposed between X and Y.

For example, in the case where X and Y are electrically connected, one or more elements that enable an electrical connection between X and Y (e.g., a switch, a transistor, a capacitor, an inductor, a resistor, a diode, a display element, a light-emitting element, or a load) can be connected between X and Y. Note that the switch is controlled to be turned on or off. That is, the switch is conducting or not conducting (is turned on or off) to determine whether current flows therethrough or not. Alternatively, the switch has a function of selecting and changing a current path. Note that the case where X and Y are electrically connected includes the case where X and Y are directly connected.

For example, in the case where X and Y are functionally connected, one or more circuits that enable functional connection between X and Y (e.g., a logic circuit such as an inverter, a NAND circuit, or a NOR circuit; a signal converter circuit such as a D/A converter circuit, an A/D converter circuit, or a gamma correction circuit; a potential level converter circuit such as a power supply circuit (e.g., a step-up circuit or a step-down circuit) or a level shifter circuit for changing the potential level of a signal; a voltage source; a current source; a switching circuit; an amplifier circuit such as a circuit that can increase signal amplitude, the amount of current, or the like, an operational amplifier, a differential amplifier circuit, a source follower circuit, and a buffer circuit; a signal generation circuit; a memory circuit; or a control circuit) can be connected between X and Y. For example, even when another circuit is interposed between X and Y, X and Y are functionally connected if a signal output from X is transmitted to Y. Note that the case where X and Y are functionally connected includes the case where X and Y are directly connected and X and Y are electrically connected.

Note that in this specification and the like, an explicit description "X and Y are connected" means that X and Y are electrically connected (i.e., the case where X and Y are connected with another element or circuit provided therebetween), X and Y are functionally connected (i.e., the case where X and Y are functionally connected with another circuit provided therebetween), and X and Y are directly connected (i.e., the case where X and Y are connected without another element or circuit provided therebetween). That is, in this specification and the like, the explicit expression "X and Y are electrically connected" is the same as the explicit simple expression "X and Y are connected".

For example, any of the following expressions can be used for the case where a source (or a first terminal or the like) of a transistor is electrically connected to X through (or not through) Z1 and a drain (or a second terminal or the like) of the transistor is electrically connected to Y through (or not through) Z2, or the case where a source (or a first terminal or the like) of a transistor is directly connected to one part of Z1 and another part of Z1 is directly connected to X while a drain (or a second terminal or the like) of the transistor is directly connected to one part of Z2 and another part of Z2 is directly connected to Y.

Examples of the expressions include, "X, Y, a source (or a first terminal or the like) of a transistor, and a drain (or a second terminal or the like) of the transistor are electrically connected to each other, and X, the source (or the first terminal or the like) of the transistor, the drain (or the second terminal or the like) of the transistor, and Y are electrically connected to each other in this order", "a source (or a first terminal or the like) of a transistor is electrically connected to X, a drain (or a second terminal or the like) of the transistor is electrically connected to Y, and X, the source (or the first terminal or the like) of the transistor, the drain (or the second terminal or the like) of the transistor, and Y are electrically connected to each other in this order", and "X is electrically connected to Y through a source (or a first terminal or the like) and a drain (or a second terminal or the like) of a transistor, and X, the source (or the first terminal or the like) of the transistor, the drain (or the second terminal or the like) of the transistor, and Y are provided to be connected in this order". When the connection order in a circuit structure is defined by an expression similar to the above examples, a source (or a first terminal or the like) and a drain (or a second terminal or the like) of a transistor can be distinguished from each other to specify the technical scope.

Other examples of the expressions include, "a source (or a first terminal or the like) of a transistor is electrically connected to X through at least a first connection path, the first connection path does not include a second connection path, the second connection path is a path between the source (or the first terminal or the like) of the transistor and a drain (or a second terminal or the like) of the transistor, Z1 is on the first connection path, the drain (or the second terminal or the like) of the transistor is electrically connected to Y through at least a third connection path, the third connection path does not include the second connection path, and Z2 is on the third connection path". It is also possible to use the expression "a source (or a first terminal or the like) of a transistor is electrically connected to X through at least Z1 on a first connection path, the first connection path does not include a second connection path, the second connection path includes a connection path through the transistor, a drain (or a second terminal or the like) of the transistor is electrically connected to Y through at least Z2 on a third connection path, and the third connection path does not include the second connection path". Still another example of the expression is "a source (or a first terminal or the like) of a transistor is electrically connected to X through at least Z1 on a first electrical path, the first electrical path does not include a second electrical path, the second electrical path is an electrical path from the source (or the first terminal or the like) of the transistor to a drain (or a second terminal or the like) of the transistor, the drain (or the second terminal or the like) of the transistor is electrically connected to Y through at least Z2 on a third electrical path, the third electrical path does not include a fourth electrical path, and the fourth electrical path is an electrical path from the drain (or the second terminal or the like) of the transistor to the source (or the first terminal or the like) of the transistor". When the connection path in a circuit structure is defined by an expression similar to the above examples, a source (or a first terminal or the like) and a drain (or a second terminal or the like) of a transistor can be distinguished from each other to specify the technical scope.

Note that one embodiment of the present invention is not limited to these expressions which are just examples. Here, each of X, Y, Z1, and Z2 denotes an object (e.g., a device, an element, a circuit, a wiring, an electrode, a terminal, a conductive film, a layer, or the like).

Even when independent components are electrically connected to each other in a circuit diagram, one component has functions of a plurality of components in some cases. For example, when part of a wiring also functions as an electrode, one conductive film functions as the wiring and the electrode. Thus, "electrical connection" in this specification includes in its category such a case where one conductive film has functions of a plurality of components.

Note that the terms "film" and "layer" can be interchanged with each other depending on the case or circumstances. For example, the term "conductive layer" can be changed into the term "conductive film" in some cases. Also, the term "insulating film" can be changed into the term "insulating layer" in some cases.

(Embodiment 1)

In this embodiment, an imaging device using radiation such as X-rays, which is one embodiment of the present invention, will be described with reference to drawings.

Figure 1B:
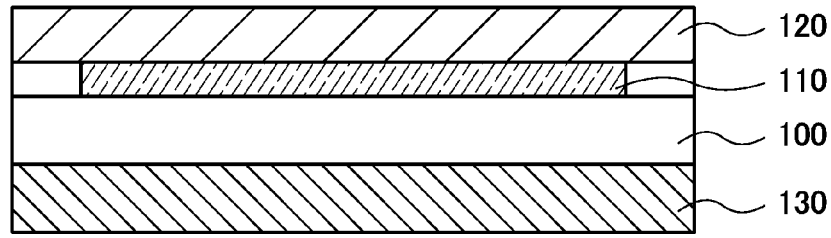

FIGS. 1A and 1B are cross-sectional views each illustrating a structure of the imaging device of one embodiment of the present invention. An imaging device 10 illustrated in FIG. 1A includes a pixel array 110 over a substrate 100, and a scintillator 120 over the pixel array 110.

The scintillator 120 is made of a substance that, when exposed to radiation such as X-rays or gamma-rays, absorbs the energy of the rays to emit visible light or ultraviolet light or a material containing the substance. Examples of the known materials include $Gd_2O_2S:Tb$, $Gd_2O_2S:Pr$, $Gd_2O_2S:Eu$, $BaFCl:Eu$, $NaI$, $CsI$, $CaF_2$, $BaF_2$, $CeF_3$, $LiF$, $LiI$, and $ZnO$, and a resin or ceramics in which any of the materials is dispersed.

Figure 2:
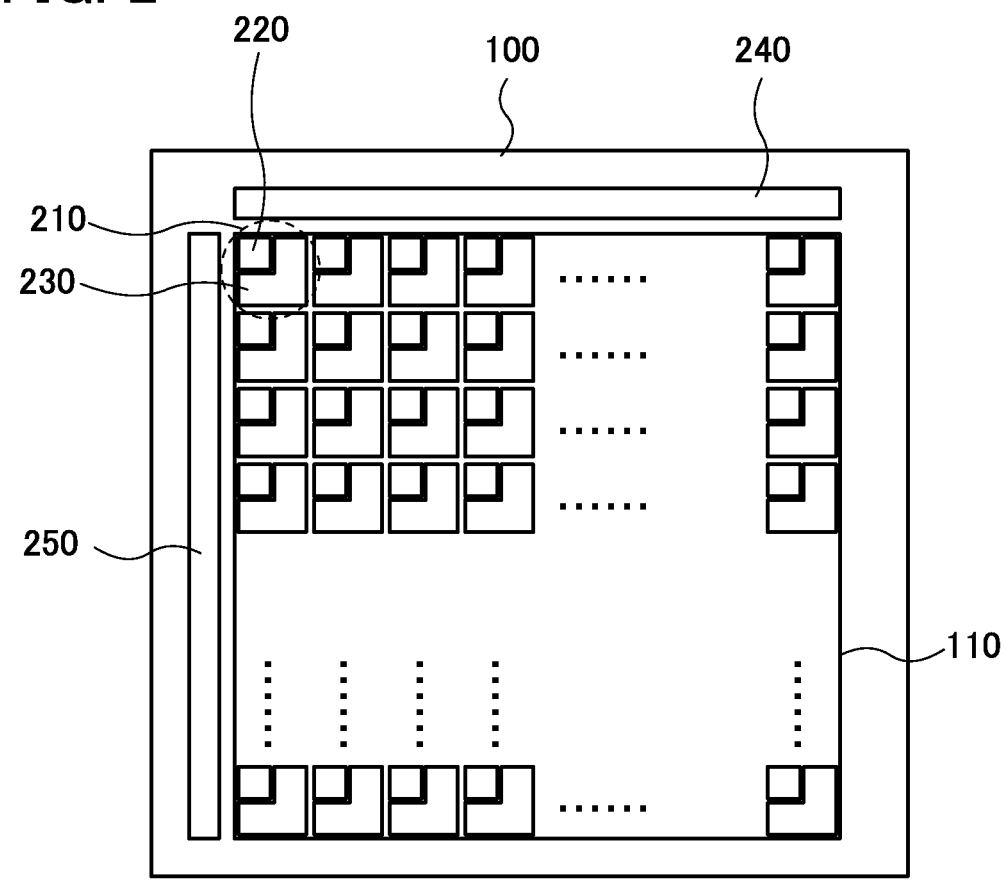
FIG. 2 is a top view of an imaging device.

The pixel array 110 over the substrate 100 can have a structure illustrated in the top view of FIG. 2, for example. Note that in FIG. 2, the scintillator 120 is omitted for clarity.

The pixel array 110 includes a plurality of pixel circuits 210 arranged in a matrix, and the pixel circuits 210 each include a light-receiving element 220 and a circuit portion 230 electrically connected to the light-receiving element 220.

In the imaging device of one embodiment of the present invention, a transistor including an oxide semiconductor in an active layer can be used for the circuit portion 230. The transistor using an oxide semiconductor has a higher mobility than a transistor using amorphous silicon, and is thus easily reduced in size, resulting in a reduction in the size of a pixel. In other words, the resolution of the imaging device can be increased.

In addition to the pixel array 110, a first circuit 240 and a second circuit 250 may be provided over the substrate 100 to drive the pixel array 110.

Although FIG. 2 shows an example in which the circuits for driving the pixel array 110 are provided in the two regions, the structures of the circuits are not limited to this example. For example, the circuits for driving the pixel array 110 may be collectively provided in one region, or may be divided into three or more parts. Furthermore, the circuits for driving the pixel array 110 may be formed directly on the substrate 100 like a transistor included in the pixel circuit 210, or may be formed by mounting an IC chip on the substrate 100 by chip on glass (COG) or the like. Alternatively, a tape carrier package (TCP), a chip on film (COF), or the like may be connected to the pixel array 110. These structures may be used in combination.

Figure 3:
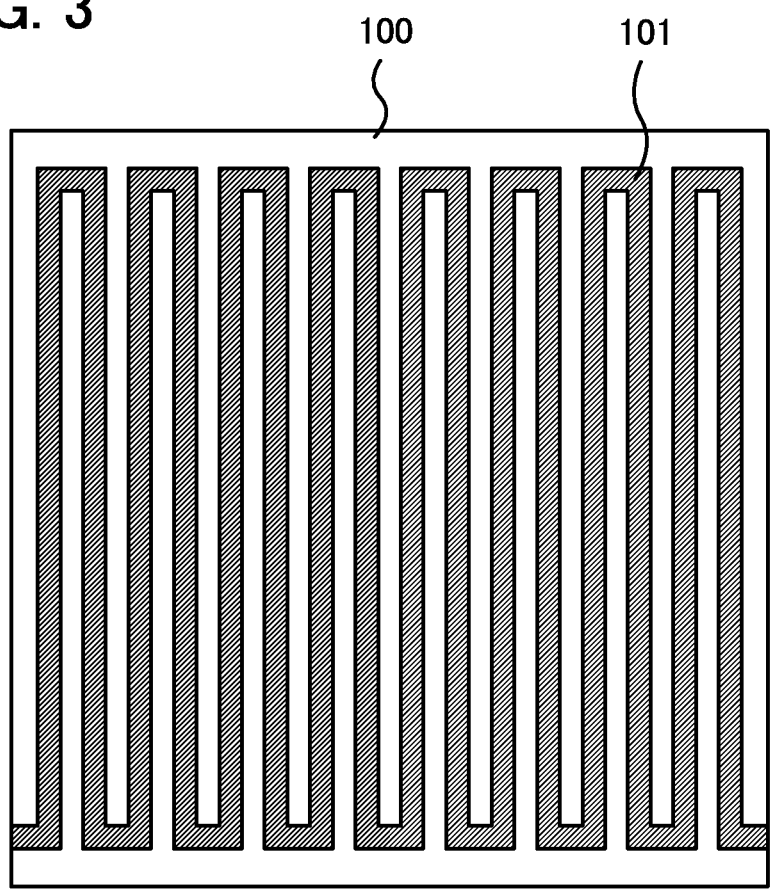
FIG. 3 illustrates a heater.

The substrate 100 is provided with a heater 101 as illustrated in FIG. 3, for example. The heater 101 can be formed using a resistor such as a metal wire or a conductive film. The passage of a current through the heater 101 produces Joule heating. The heater 101 may be formed on either surface of the substrate 100 or embedded in the substrate 100. Note that the shape of the heater 101 is not limited to that illustrated in FIG. 3 which is just an example. In the imaging device of one embodiment of the present invention, the substrate 100 including the heater 101 needs to have a high light-transmitting property in some cases. In that case, a light-transmitting resistor is preferably used as the heater 101. For example, a metal or a nitride such as tungsten, chromium, titanium, titanium nitride, or tantalum nitride, or an oxide such as zinc oxide, tin oxide, or indium oxide can be used for the heater 101.

The imaging device of one embodiment of the present invention may have a structure illustrated in FIG. 1B. An imaging device 20 has a structure in which a light-emitting device 130 is provided in contact with the substrate 100 of the imaging device 10 illustrated in FIG. 1A. A light-emitting diode or the like can be used as a light source of the light-emitting device 130.

Radiation such as X-rays passes through a subject to enter the scintillator 120, and then is converted into light (fluorescence) such as visible light or ultraviolet light owing to a phenomenon known as photoluminescence. The light is sensed by the light-receiving element 220 provided in the pixel circuit 210, whereby image data is obtained.

Note that part of the radiation emitted to the scintillator 120 is not used for photoluminescence but passes through the scintillator 120. If a semiconductor material or an insulating material of a transistor is exposed to the radiation such as X-rays, defect states and the like are generated in the irradiated portion, whereby the electrical characteristics of the transistor change. This might lead to increased power consumption or decreased reliability of the imaging device.

For example, if a transistor including an oxide semiconductor in its channel formation region and including a silicon oxide film as a gate insulating film is irradiated with intense X-rays in an accelerated test, the threshold voltage of the transistor shifts in the negative direction.

Figure 4:
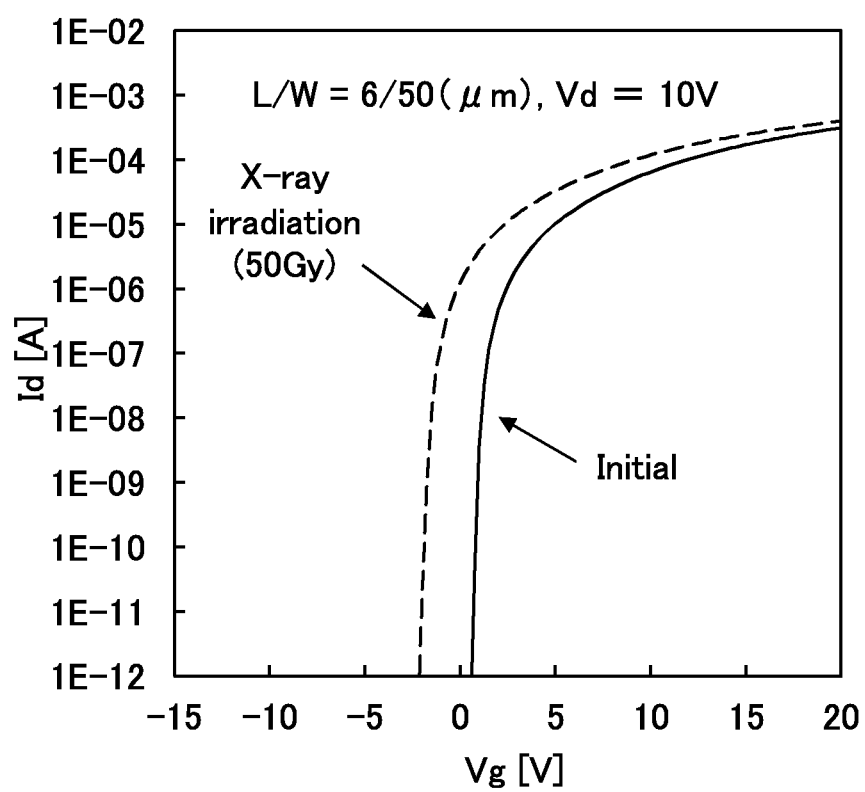
FIG. 4 shows Id–Vg characteristics of a transistor before and after X-ray irradiation.

FIG. 4 shows an example of the Id–Vg characteristics (Vd=10 V) of a transistor using an oxide semiconductor for an active layer before and after X-ray irradiation. The transistor has a bottom-gate structure in which an oxide semiconductor is used for an active layer and a stack of a silicon nitride film and a silicon oxide film is used for a gate insulating film. The L/W of the transistor is 6/50 μm.

In the initial state, the transistor has a low off-state current and exhibits excellent normally-off characteristics. After X-ray irradiation (50 Gy), the gate voltage (Vg) at which a current starts flowing largely shifts in the negative direction. The amount of shift in the threshold voltage of the transistor (ΔVth) is −2.6 V, and the amount of shift in the shift value (ΔShift) is −2.7 V. In this specification, the shift value (Shift) is defined as the gate voltage (Vg) at the time when Id=1×10$^{-12}$ [A] is satisfied. Note that a top-gate transistor also degrades in the same way.

The following is a degradation model in X-ray irradiation. First, by X-ray irradiation, an electron-hole is generated in an oxide semiconductor (an active layer of the transistor, e.g., an In—Ga—Zn oxide layer). Next, the generated hole is trapped in a deep defect state in the oxide semiconductor which is derived from an oxygen vacancy. Then, the trapped hole is injected into a defect state of a non-bridging oxygen hole center (NBOHC) in silicon oxide (the gate insulating film of the transistor). The injected hole serves as a fixed charge having a positive charge in silicon oxide, thereby changing the threshold voltage of the transistor.

Figure 5:
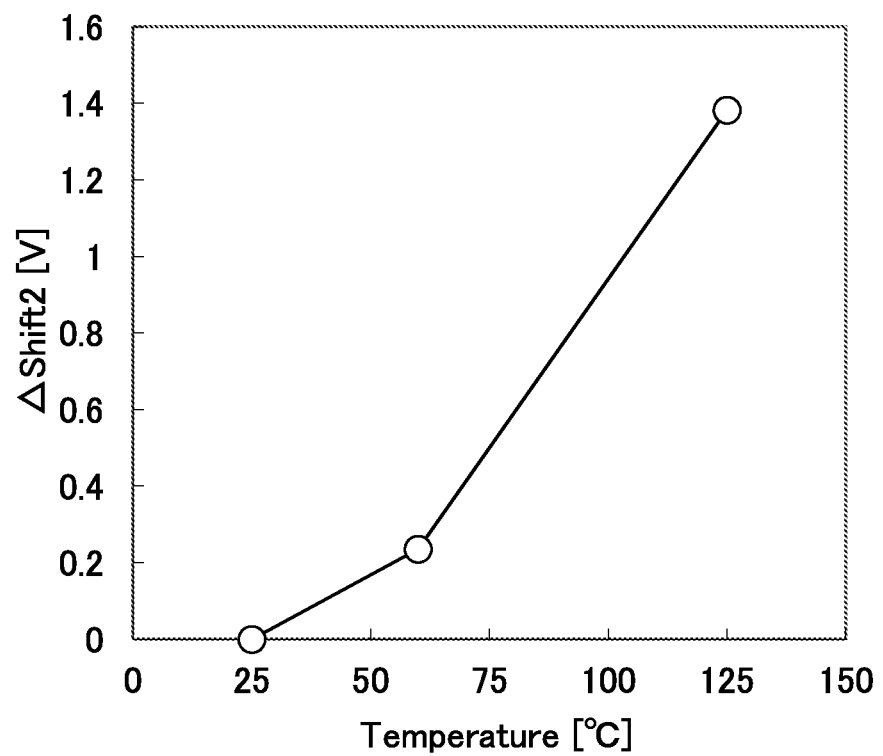
FIG. 5 shows the amount of returned shift value calculated from the Id–Vg characteristics after heat treatment.

Such a degraded transistor is subjected to heat treatment. Then, the gate voltage (Vg) at which a current starts flowing shifts in the positive direction. FIG. 5 shows the amount of returned shift value (ΔShift2) calculated from the Id–Vg characteristics after the heat treatment. A point plotted at 25° C. shows the result of a sample that was not subjected to heat treatment, and points plotted at 60° C. and 125° C. show the results of samples that were heated at the respective temperatures for 30 minutes. FIG. 5 shows that the shift value is returned more easily when the heat treatment is performed at higher temperatures.

Figure 6:
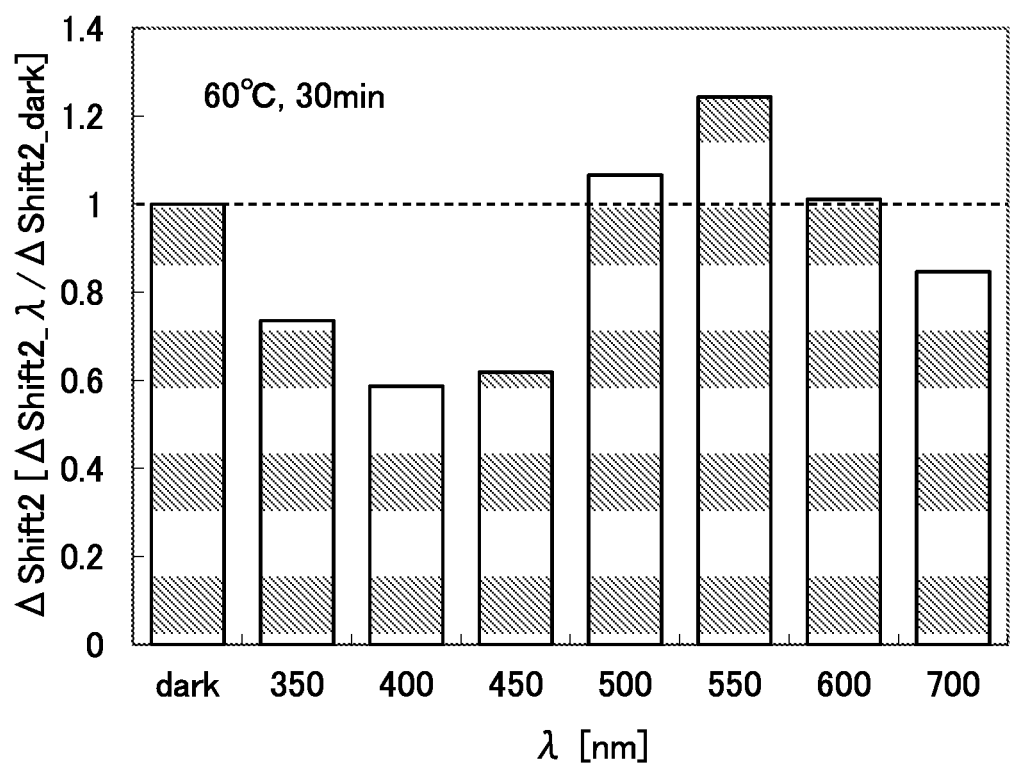
FIG. 6 shows the amount of returned shift value calculated from the Id–Vg characteristics after heat treatment and light irradiation.

FIG. 6 shows the amount of returned shift value (ΔShift2) of a degraded transistor that was subjected to heat treatment and light irradiation, which was calculated from the Id—Vg characteristics. The heat treatment was performed at 60° C. and light irradiation with each wavelength was performed for 30 minutes. Note that dark denotes a sample that was subjected only to heat treatment without light irradiation. The longitudinal axis represents a normalized value with the value of dark taken as 1.

FIG. 6 indicates that degradation due to light irradiation can be recovered when the amount of returned shift value (ΔShift2) is larger than that of dark. Specifically, light with a wavelength of 500 nm to 600 nm, more preferably, approximately 550 nm are preferably emitted. The heat treatment and light in the above wavelength range significantly contribute to a reduction in fixed charges in the gate insulating film. That is, the heat and light do not produce another source of degradation and can supply the activation energy necessary for recovery of degradation.

In contrast, irradiation with light with a wavelength shorter than 500 nm or longer than 600 nm hardly contributes to a reduction in the fixed charges, produces another source of degradation, or temporarily generates a photocurrent that causes a negative shift of the Id–Vg characteristics; as a result, the amount of returned shift value gets small.

Thus, degradation due to X-ray irradiation can be recovered by adjusting the temperature and time of heat treatment. Alternatively, degradation due to X-ray irradiation can be recovered by irradiation with light with a wavelength of 500 nm to 600 nm. Further alternatively, degradation due to X-ray irradiation can be recovered by combining heat treatment and light irradiation. Note that heat treatment at high temperatures requires cooling measures or countermeasures against heat to prevent damage on the components and circumference of the imaging device. It is therefore preferable that heat treatment at low temperatures be combined with light irradiation to recover degradation due to X-ray irradiation. For example, heat treatment is performed at temperatures of approximately 60° C. to 80° C. and light with a wavelength of approximately 550 nm is emitted. In such a case, degradation in X-ray irradiation can be recovered rapidly without a need of extensive cooling measures or countermeasures against heat.

From the above experimental results, the inventors have proposed the imaging devices illustrated in FIGS. 1A and 1B. In the imaging device 10 illustrated in FIG. 1A, heat treatment is performed on the pixel array 110 with use of the heater on the substrate 100, thereby recovering the electrical characteristics of the transistor degraded by X-ray irradiation. If cooling measures or countermeasures against heat are taken properly, the pixel array 110 may be heated at temperatures higher than or equal to 100° C.

In the imaging device 20 illustrated in FIG. 1B, heat treatment is performed on the pixel array 110 with use of the heater 101 on the substrate 100, and light is emitted from the light-emitting device 130 to the pixel array 110, thereby recovering the electrical characteristics of the transistor degraded by X-ray irradiation. If cooling measures or countermeasures against heat are taken properly, the pixel array 110 may be heated at temperatures higher than or equal to 100° C. Light emitted from the light-emitting device 130 may be monochromatic light with a wavelength of 500 nm to 600 nm or a mixture of colors including light in this wavelength range. Note that the transistor included in the pixel array 110 preferably has a top-gate structure so that light from the light-emitting device 130 is effectively emitted to an active layer of the transistor.

In the imaging devices 10 and 20 of one embodiment of the present invention, the heat treatment on the pixel array 110 with use of the heater 101 and the light irradiation to the pixel array 110 with use of the light-emitting device 130 are preferably performed at times other than imaging. If the heat treatment is performed on the pixel array 110 at the time of imaging, the off-state current of the transistor increases to decrease dynamic range. When light is emitted from the light-emitting device 130, the light is sensed by the light-receiving element 220 and thus imaging is hindered. Thus, the heat treatment and light irradiation are preferably performed at waiting time, for example, between an interval of imaging. Alternatively, by using a timer or the like, the heat treatment and light irradiation may be performed at the time when an imaging system including the imaging device is turned on or off. The imaging system may have a means (such as an air blower) for cooling the imaging device so that images can be taken rightly after the heat treatment.

It is thus possible to provide an imaging device that is highly stable when exposed to radiation such as X-rays and whose electrical characteristics can be prevented from decreasing.

Figure 17A:
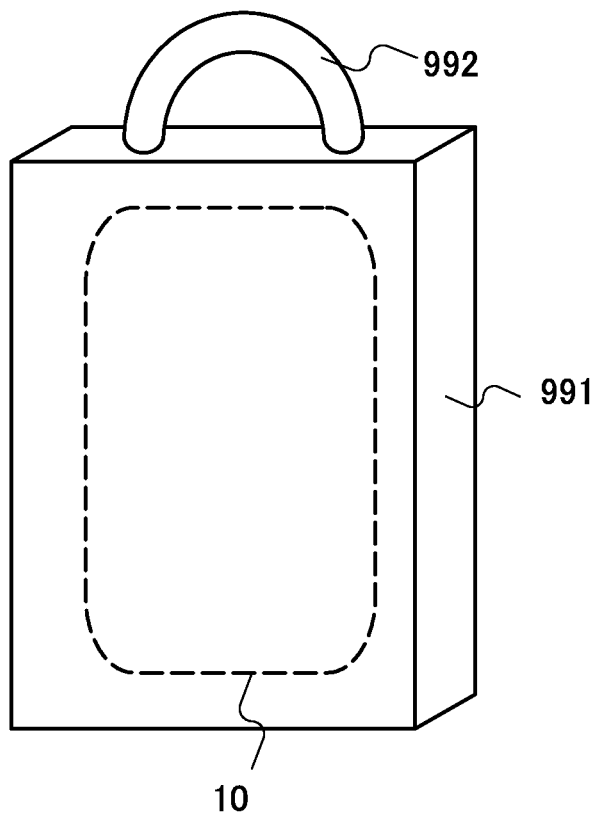
FIGS. 17A and 17B illustrate a structure of an imaging system.

FIG. 17A illustrates an example of a detector unit including the imaging device 10 or 20. A detector unit 991 is provided with a handle 992. In some cases, the detector unit 991 includes not only the imaging device of one embodiment of the present invention but also part or whole of the peripheral equipment of the imaging device.

Figure 17B:
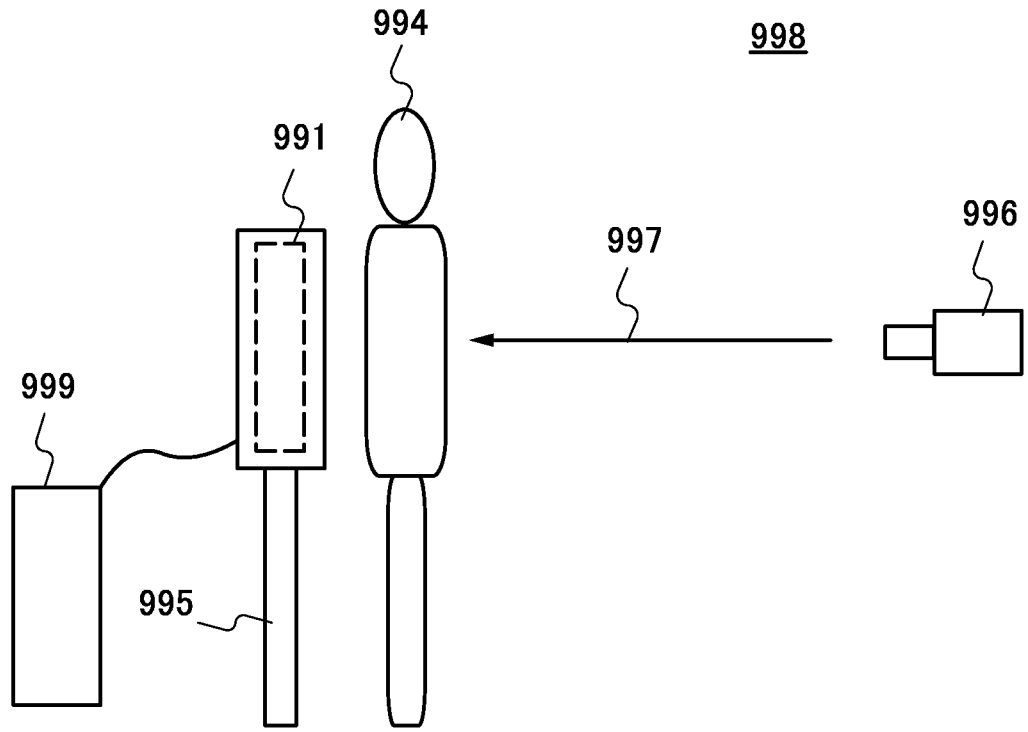

FIG. 17B illustrates an example of the entire structure of an imaging system 998. The detector unit 991 is placed on a stand 995. The detector unit 991 is connected to a computer 999 in some cases. An X-ray 997 emitted from an X-ray source 996 passes through a subject 994 and is sensed by the detector unit 991.

This embodiment can be implemented in an appropriate combination with any of the structures described in the other embodiments.

(Embodiment 2)

In this embodiment, the pixel circuit 210 shown in Embodiment 1 will be described.

Figure 7A:
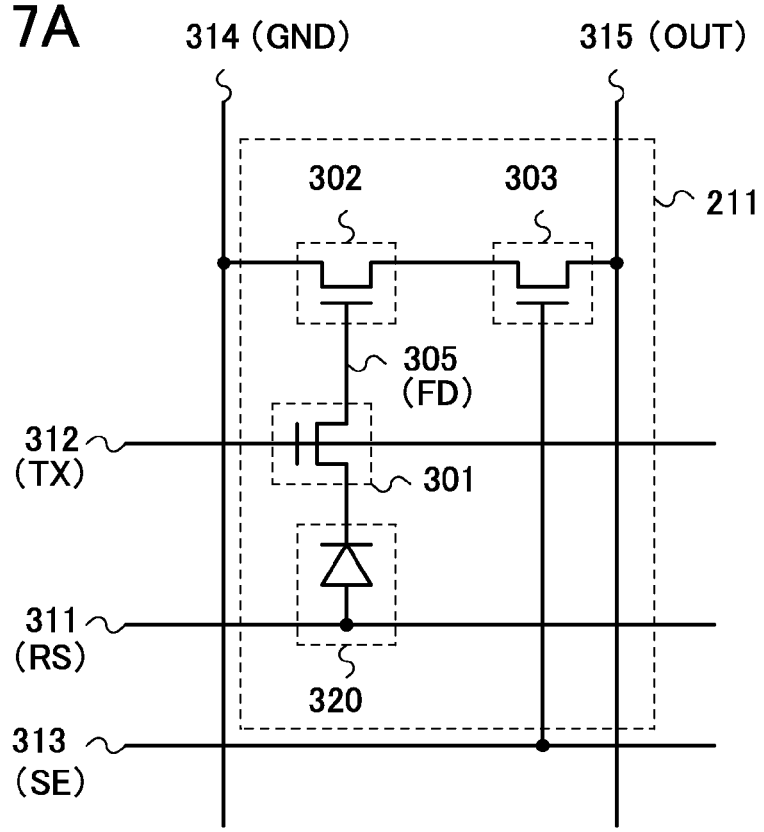
FIGS. 7A and 7B each illustrate a configuration of a pixel circuit.

FIG. 7A shows an example of a circuit that can be used as the pixel circuit 210 illustrated in FIG. 2. A circuit 211 includes a photodiode 320 serving as the light-receiving element 220, and a first transistor 301, a second transistor 302, and a third transistor 303 that are provided in the circuit portion 230 connected to the light-receiving element 220.

An anode of the photodiode 320 is electrically connected to a first wiring 311 (RS); a cathode of the photodiode 320 is electrically connected to one of a source and a drain of the first transistor 301; the other of the source and the drain of the first transistor 301 is electrically connected to a wiring 305 (FD); a gate of the first transistor 301 is electrically connected to a second wiring 312 (TX); one of a source and a drain of the second transistor 302 is electrically connected to a fourth wiring 314 (GND); the other of the source and the drain of the second transistor 302 is electrically connected to one of a source and a drain of the third transistor 303; a gate of the second transistor 302 is electrically connected to the wiring 305 (FD); the other of the source and the drain of the third transistor 303 is electrically connected to a fifth wiring 315 (OUT); and a gate of the third transistor 303 is electrically connected to a third wiring 313 (SE).

A potential such as GND, VSS, or VDD may be supplied to the fourth wiring 314. Here, a potential or a voltage has a relative value. Therefore, the potential GND is not necessarily 0 V.

The photodiode 320 is a light-receiving element and generates a current corresponding to the amount of light entering the pixel circuit. The first transistor 301 controls accumulation in the wiring 305 (FD) of electrical charges generated by the photodiode 320. A signal corresponding to a potential of the wiring 305 (FD) is output from the second transistor 302. The third transistor 303 controls the selection of the pixel circuit at the time of reading.

Note that the wiring 305 (FD) is a charge accumulation portion retaining electrical charges whose amount changes depending on the amount of light received by the photodiode 320. Practically, the charge accumulation portion is depletion layer capacitance in the vicinity of a source region or a drain region of the first transistor 301 electrically connected to the wiring 305 (FD), wiring capacitance of the wiring 305 (FD), gate capacitance of the second transistor 302 electrically connected to the wiring 305 (FD), and the like.

Note that the second transistor 302 and the third transistor 303 only need to be connected in series between the fifth wiring 315 and the fourth wiring 314. Hence, the fourth wiring 314, the second transistor 302, the third transistor 303, and the fifth wiring 315 may be arranged in order, or the fourth wiring 314, the third transistor 303, the second transistor 302, and the fifth wiring 315 may be arranged in order.

The first wiring 311 (RS) is a signal line for resetting the wiring 305 (FD). The first wiring 311 (RS) in the circuit 211 is also a signal line for performing charge accumulation in the wiring 305 (FD). The second wiring 312 (TX) is a signal line for controlling the first transistor 301. The third wiring 313 (SE) is a signal line for controlling the third transistor 303. The fourth wiring 314 (GND) is a signal line for setting a reference potential (e.g., GND). The fifth wiring 315 (OUT) is a signal line for reading data obtained in the circuit 211.

Figure 7B:
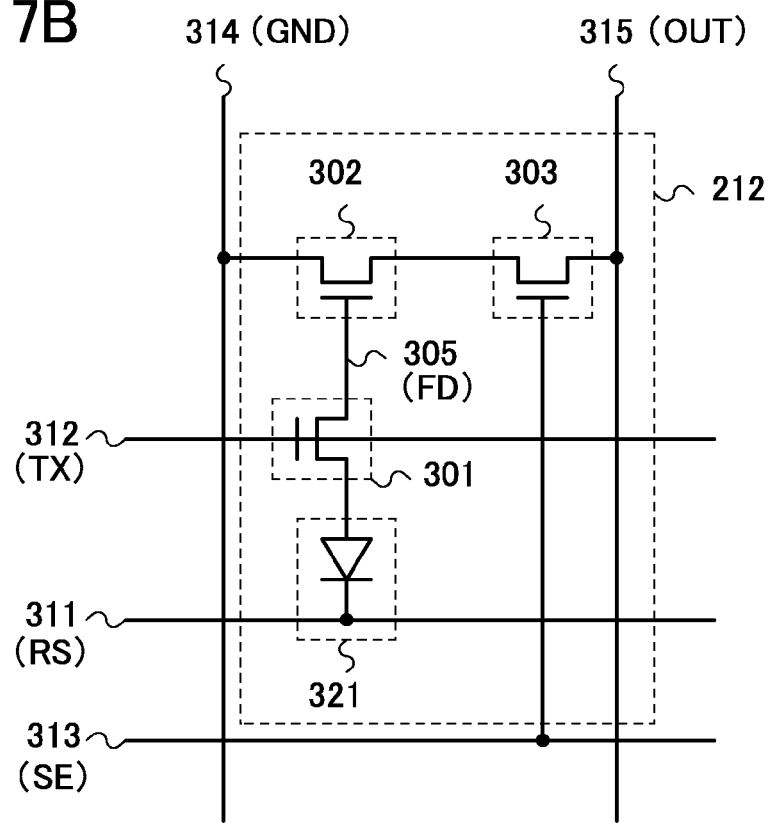

The pixel circuit 210 may have a configuration illustrated in FIG. 7B. A circuit 212 illustrated in FIG. 7B includes the same components as those in the circuit 211 in FIG. 7A but is different from the circuit 211 in that an anode of a photodiode 321 is electrically connected to one of the source and the drain of the first transistor 301 and a cathode of the photodiode 321 is electrically connected to the first wiring 311 (RS).

Next, a structure of each component illustrated in FIGS. 7A and 7B will be described.

The photodiodes 320 and 321 can be formed using a silicon semiconductor with a pn junction or a pin junction, for example. In the case where a scintillator emits visible light, a pin photodiode including an i-type semiconductor layer formed of amorphous silicon is preferably used. Since amorphous silicon has a high sensitivity in a visible light wavelength region, weak visible light can be sensed easily.

Note that the i-type semiconductor refers not only to what is called an intrinsic semiconductor in which the Fermi level lies in the middle of the band gap, but also to a semiconductor in which the concentration of an impurity imparting p-type conductivity and the concentration of an impurity imparting n-type conductivity are less than or equal to $1 \times 10^{20}$ atoms/$cm^3$ and in which the photoconductivity is higher than the dark conductivity.

Although a silicon semiconductor such as amorphous silicon, microcrystalline silicon, polycrystalline silicon, or single crystal silicon can be used to form the first transistor 301, the second transistor 302, and the third transistor 303, an oxide semiconductor is preferably used to form the transistors. A transistor including an oxide semiconductor in a channel formation region has an extremely low off-state current.

In particular, when the first transistor 301 connected to the wiring 305 (FD) has a high leakage current, electrical charges accumulated in the wiring 305 (FD) cannot be retained for a sufficiently long time. The use of an oxide semiconductor for the first transistor 301 prevents unwanted output of electrical charges through the photodiode 320.

Unwanted output of electrical charges also occurs in the fourth wiring 314 or the fifth wiring 315 when the second transistor 302 and the third transistor 303 have a high leakage current; thus, each of these transistors is also preferably a transistor including an oxide semiconductor in a channel formation region.

When the transistor using an oxide semiconductor with an extremely low off-state current is used as the second transistor 302, imaging can be performed with wider dynamic range. In the pixel circuit illustrated in FIG. 7A, a gate potential of the second transistor 302 is decreased with an increase in the intensity of light entering the photodiode 320. In the pixel circuit illustrated in FIG. 7B, the gate potential of the second transistor 302 is decreased with a decrease in the intensity of light entering the photodiode 321. Since the transistor using an oxide semiconductor has an extremely low off-state current, a current corresponding to the gate potential can be accurately output even when the gate potential is extremely low. Thus, it is possible to broaden the detection range of illuminance, i.e., the dynamic range.

Also in the pixel circuit illustrated in FIG. 7B, a sufficiently wide dynamic range can be obtained even when the gate potential of the second transistor 302 is relatively low, i.e., when the intensity of light emitted from the scintillator to the photodiode 321 is low. In other words, the scintillator does not need to emit high-intensity light, which makes it possible to reduce the intensity of X-rays emitted to a subject.

Next, an example of the operation of the circuit 211 in FIG. 7A will be described with reference to the timing chart in FIG. 8A.

Figure 8A:
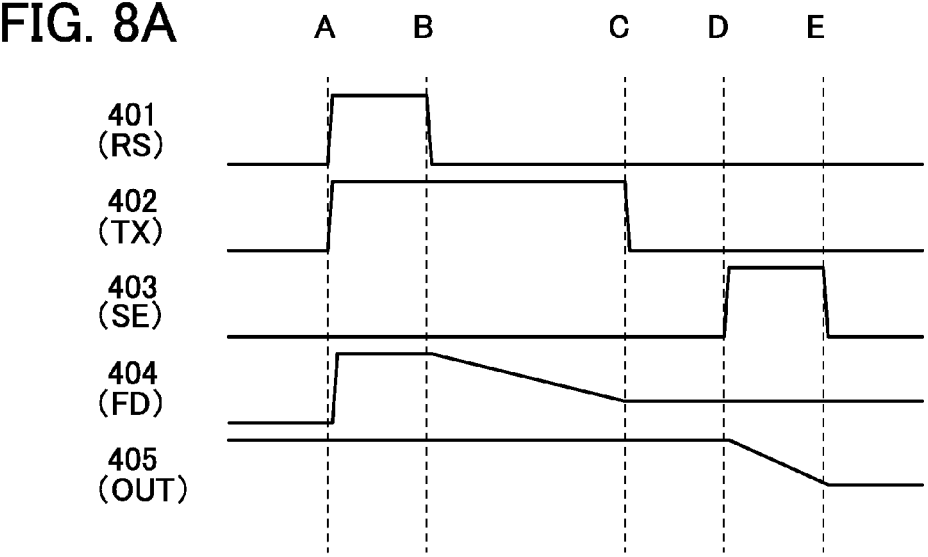
FIGS. 8A to 8C are timing charts each showing the operation of a pixel circuit.

In FIG. 8A, a signal which varies between two levels is applied to each wiring, for simplicity. Note that in practice, an analog signal is input; hence, the potential can have various levels depending on the circumstances without being limited to two levels. In the timing chart, a signal 401 corresponds to the potential of the first wiring 311 (RS); a signal 402, the potential of the second wiring 312 (TX); a signal 403, the potential of the third wiring 313 (SE); a signal 404, the potential of the wiring 305 (FD); and a signal 405, the potential of the fifth wiring 315 (OUT).

At time A, the potential of the first wiring 311 (signal 401) is set high and the potential of the second wiring 312 (signal 402) is set high, whereby a forward bias is applied to the photodiode 320 and the potential of the wiring 305 (signal 404) is set high. In other words, the potential of the charge accumulation portion is initialized to the potential of the first wiring 311 and brought into a reset state. The above is the start of a reset operation. Note that the potential of the fifth wiring 315 (signal 405) is precharged to high.

At time B, the potential of the first wiring 311 (signal 401) is set low and the potential of the second wiring 312 (signal 402) is set high, so that the reset operation is terminated and an accumulation operation starts. Here, a reverse bias is applied to the photodiode 320, whereby the potential of the wiring 305 (signal 404) starts to decrease due to a reverse current. Since irradiation of the photodiode 320 with light increases the reverse current, the rate of decrease in the potential of the wiring 305 (signal 404) changes depending on the amount of the light irradiation. In other words, channel resistance between the source and the drain of the second transistor 302 changes depending on the amount of light emitted to the photodiode 320.

Note that the light emitted to the photodiode 320 refers to the light which is converted from radiation such as X-rays by the scintillator.

At time C, the potential of the second wiring 312 (signal 402) is set low to terminate the accumulation operation, so that the potential of the wiring 305 (signal 404) becomes constant. Here, the potential is determined by the number of electrical charges generated by the photodiode 320 during the accumulation operation. That is, the potential changes depending on the amount of light emitted to the photodiode 320. Furthermore, the first transistor 301 includes a channel formation region in an oxide semiconductor layer and thus has an extremely low off-state current. Accordingly, the potential of the wiring 305 can be kept constant until a subsequent selection operation (read operation) is performed.

Note that when the potential of the second wiring 312 (signal 402) is set low, the potential of the wiring 305 changes due to parasitic capacitance between the second wiring 312 and the wiring 305 in some cases. In the case where this potential change is large, the number of electrical charges generated by the photodiode 320 during the accumulation operation cannot be obtained accurately. Examples of effective measures to decrease the potential change include reducing the capacitance between the gate and the source (or between the gate and the drain) of the first transistor 301, increasing the gate capacitance of the second transistor 302, and providing a storage capacitor connected to the wiring 305. Note that in this embodiment, the potential change can become negligible by the adoption of these measures.

At time D, the potential of the third wiring 313 (signal 403) is set high to turn on the third transistor 303, whereby the selection operation starts and the fourth wiring 314 and the fifth wiring 315 are electrically connected to each other through the second transistor 302 and the third transistor 303. Also, the potential of the fifth wiring 315 (signal 405) starts to decrease. Note that precharge of the fifth wiring 315 is terminated before time D. Here, the rate of decrease in the potential of the fifth wiring 315 (signal 405) depends on the current between the source and the drain of the second transistor 302. That is, the rate of decrease changes depending on the amount of light emitted to the photodiode 320 during the accumulation operation.

At time E, the potential of the third wiring 313 (signal 403) is set low to turn off the third transistor 303, so that the selection operation is terminated and the potential of the fifth wiring 315 (signal 405) becomes a constant value. Here, the constant value depends on the amount of light emitted to the photodiode 320. Therefore, the amount of light emitted to the photodiode 320 during the accumulation operation can be found by obtaining the potential of the fifth wiring 315.

More specifically, the stronger the light emitted to the photodiode 320 is, the lower the potential of the wiring 305 is and the lower a gate voltage of the second transistor 302 is, resulting in a gradual decrease in the potential of the fifth wiring 315 (signal 405). Thus, a relatively high potential can be read from the fifth wiring 315.

Conversely, the weaker the light emitted to the photodiode 320 is, the higher the potential of the wiring 305 is and the higher the gate voltage of the second transistor 302 is, resulting in a rapid decrease in the potential of the fifth wiring 315 (signal 405). Thus, a relatively low potential can be read from the fifth wiring 315.

Next, an example of the operation of the circuit 212 in FIG. 7B will be described with reference to the timing chart in FIG. 8B.

At time A, the potential of the first wiring 311 (signal 401) is set low and the potential of the second wiring 312 (signal 402) is set high, whereby a forward bias is applied to the photodiode 321 and the potential of the wiring 305 (signal 404) is set low. In other words, the potential of the charge accumulation portion is brought into a reset state. The above is the start of a reset operation. Note that the potential of the fifth wiring 315 (signal 405) is precharged to high.

At time B, the potential of the first wiring 311 (signal 401) is set high and the potential of the second wiring 312 (signal 402) is set high, so that the reset operation is terminated and an accumulation operation starts. Here, a reverse bias is applied to the photodiode 321, whereby the potential of the wiring 305 (signal 404) starts to increase due to a reverse current. Since irradiation of the photodiode 321 with light increases the reverse current, the rate of increase in the potential of the wiring 305 (signal 404) changes depending on the amount of the light irradiation. In other words, channel resistance between the source and the drain of the second transistor 302 changes depending on the amount of light emitted to the photodiode 321.

The description of the timing chart in FIG. 8A can be referred to for the operations at and after time C. The amount of light emitted to the photodiode 321 during the accumulation operation can be found by obtaining the potential of the fifth wiring 315 at time E.

Figure 9A:
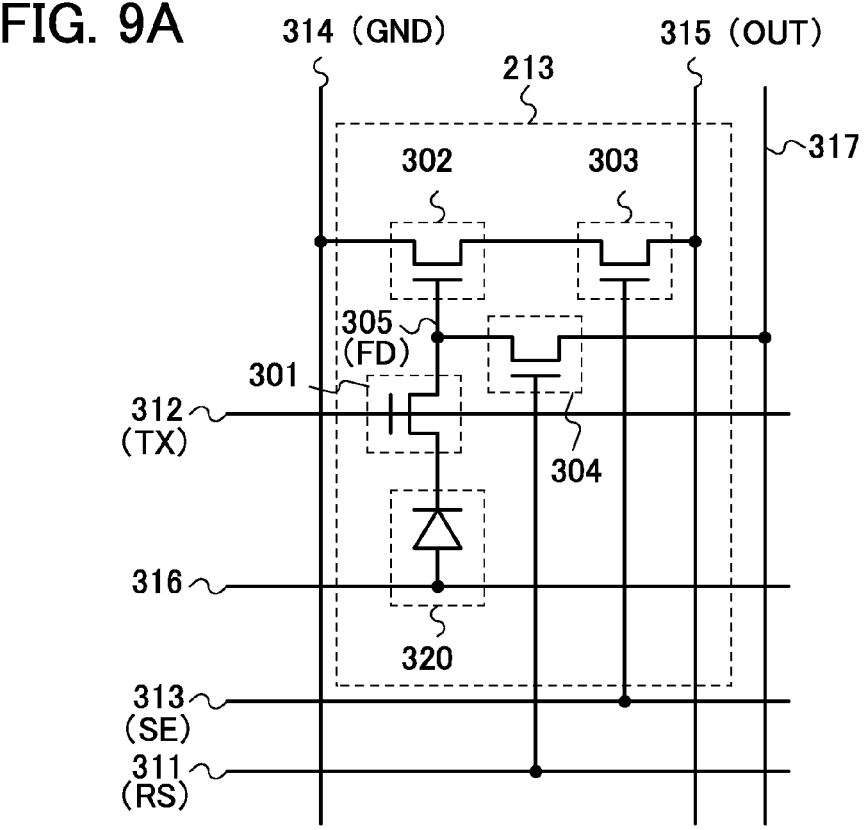
FIGS. 9A and 9B each illustrate a configuration of a pixel circuit.
Figure 9B:
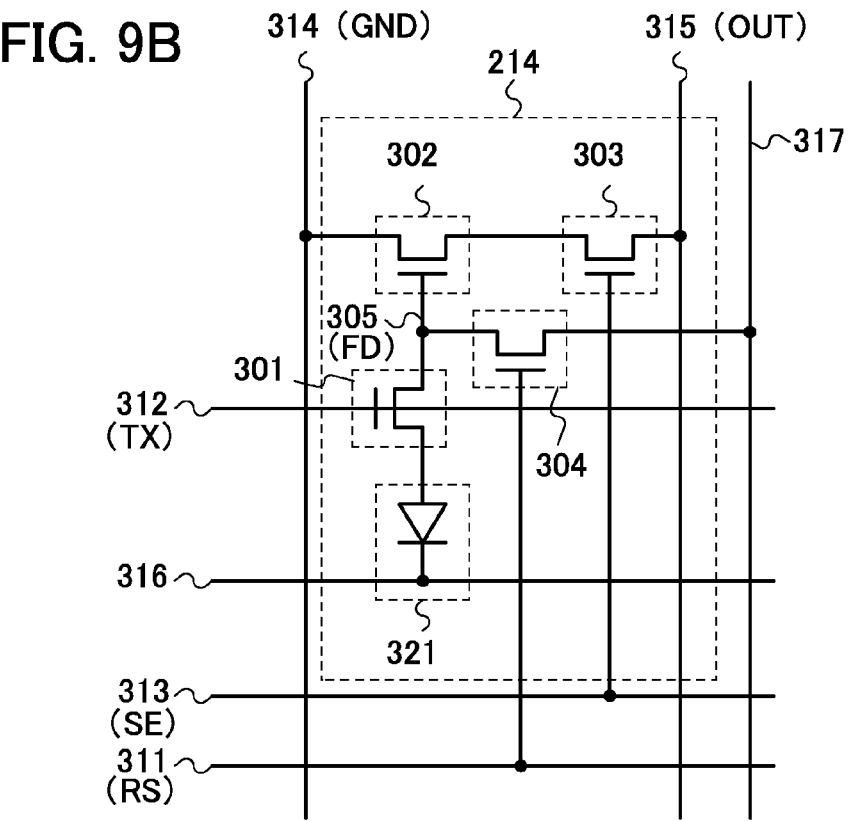

The pixel circuit 210 may have a configuration illustrated in FIG. 9A or 9B.

A circuit 213 illustrated in FIG. 9A has a configuration in which a fourth transistor 304 is added to the circuit 211 in FIG. 7A. A gate of the transistor 304 is electrically connected to the first wiring 311; one of a source and a drain of the transistor 304 is electrically connected to the wiring 305 (FD); the other of the source and the drain of the transistor 304 is electrically connected to a seventh wiring 317; and the anode of the photodiode 320 is electrically connected to a sixth wiring 316. Here, the sixth wiring 316 is a signal line (low potential line) for applying a reverse bias to the photodiode 320 all the time. The seventh wiring 317 is a signal line (high potential line) for resetting the wiring 305 to a high potential.

The fourth transistor 304 serves as a reset transistor for resetting the wiring 305 (FD). Hence, unlike in the circuit 211 in FIG. 7A, the reset operation using the photodiode 320 is not performed and a reverse bias is applied to the photodiode all the time. The wiring 305 (FD) can be reset by setting the potential of the first wiring 311 (RS) high. Operations of the circuit 213 are the same as those of the circuit 211 in FIG. 7A, which are illustrated in the timing chart in FIG. 8A.

Figure 8B:
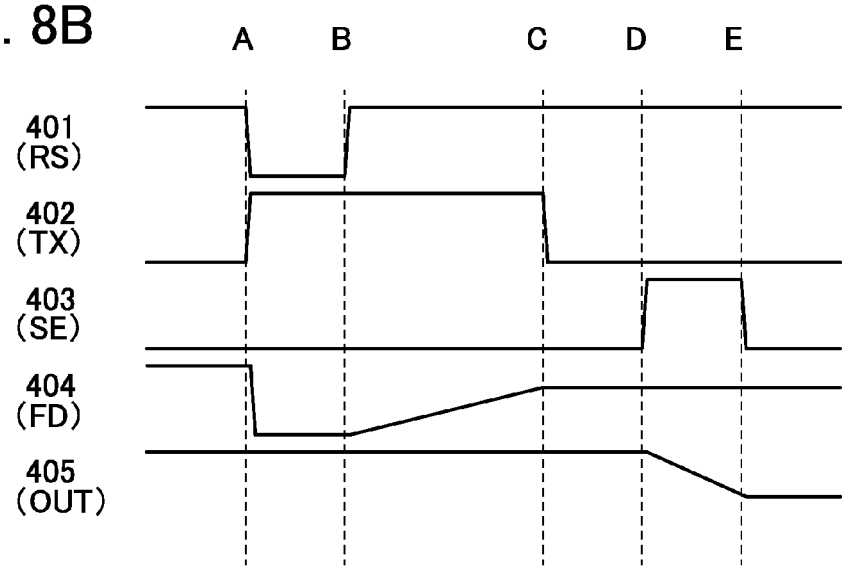

A circuit 214 illustrated in FIG. 9B has a configuration in which the fourth transistor 304 is added to the circuit 212 in FIG. 8B. The gate of the transistor 304 is electrically connected to the first wiring 311; one of the source and the drain of the transistor 304 is electrically connected to the wiring 305 (FD); the other of the source and the drain of the transistor 304 is electrically connected to the seventh wiring 317; and the cathode of the photodiode 321 is electrically connected to the sixth wiring 316. Here, the sixth wiring 316 is a signal line (high potential line) for applying a reverse bias to the photodiode 321 all the time. The seventh wiring 317 is a signal line (low potential line) for resetting the wiring 305 to a low potential.

Figure 8C:
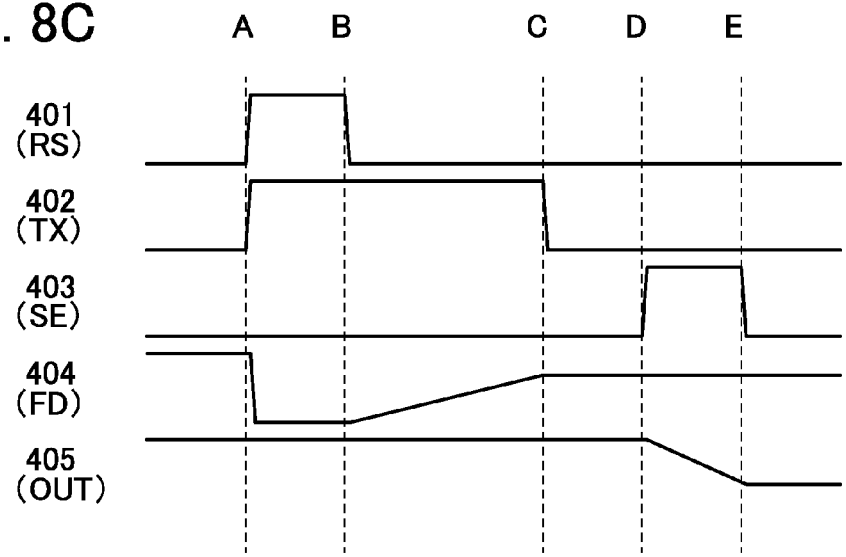

The fourth transistor 304 serves as a reset transistor for resetting the wiring 305 (FD). Hence, unlike in the circuit 212 in FIG. 7B, the reset operation using the photodiode 321 is not performed and a reverse bias is applied to the photodiode 321 all the time. The wiring 305 (FD) can be reset by setting the potential of the first wiring 311 (RS) high. The circuit 214 can operate in accordance with the timing chart in FIG. 8C.

Figure 18A:
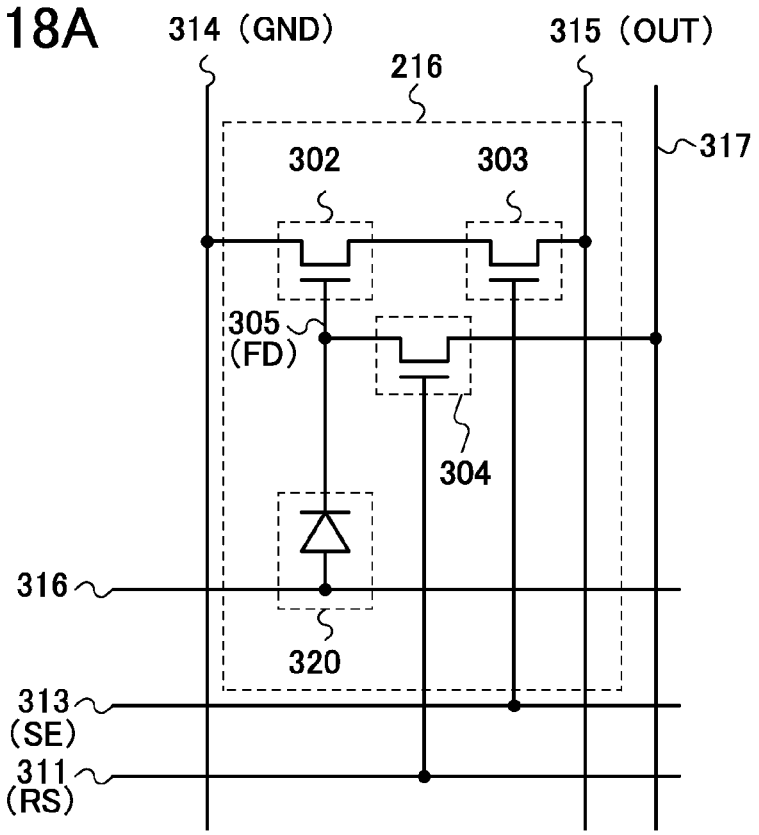
FIGS. 18A and 18B each illustrate a configuration of a pixel circuit.
Figure 18B:
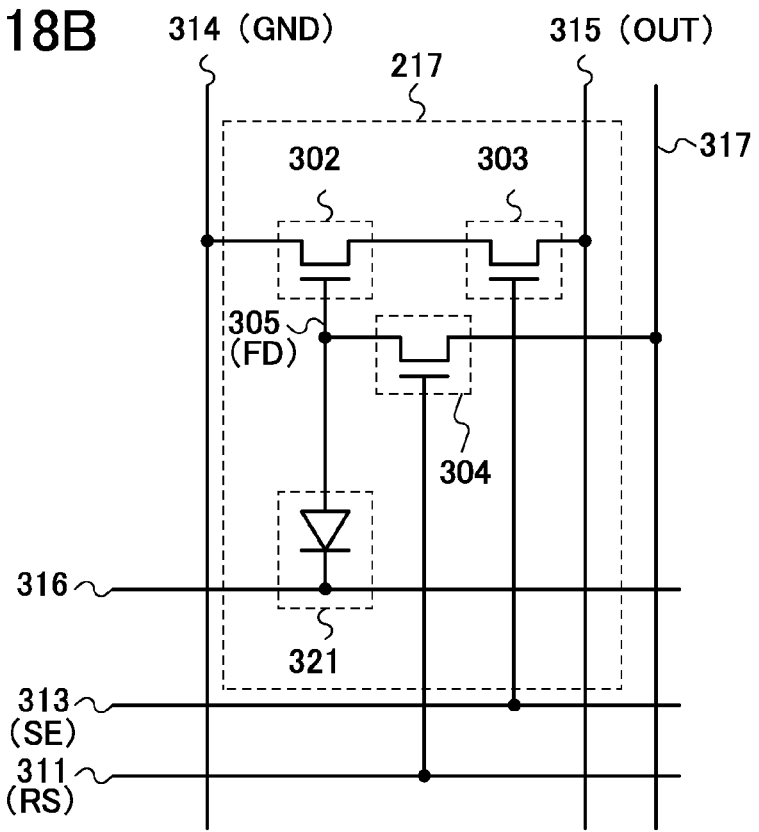

FIGS. 9A and 9B each show, but are not limited to, an example including the first transistor 301. Circuits 216 and 217 illustrated in FIGS. 18A and 18B have configurations in which the first transistor 301 is omitted from the circuits 213 and 214 in FIGS. 9A and 9B.

The fourth transistor 304 can be formed using a silicon semiconductor such as amorphous silicon, microcrystalline silicon, polycrystalline silicon, or single crystal silicon; however, when the fourth transistor 304 has a high leakage current, electrical charges cannot be retained in the charge accumulation portion for a sufficiently long time. For this reason, a transistor formed using an oxide semiconductor with an extremely low off-state current is preferably used as the fourth transistor 304, as in the case of the first transistor 301.

Figure 10:
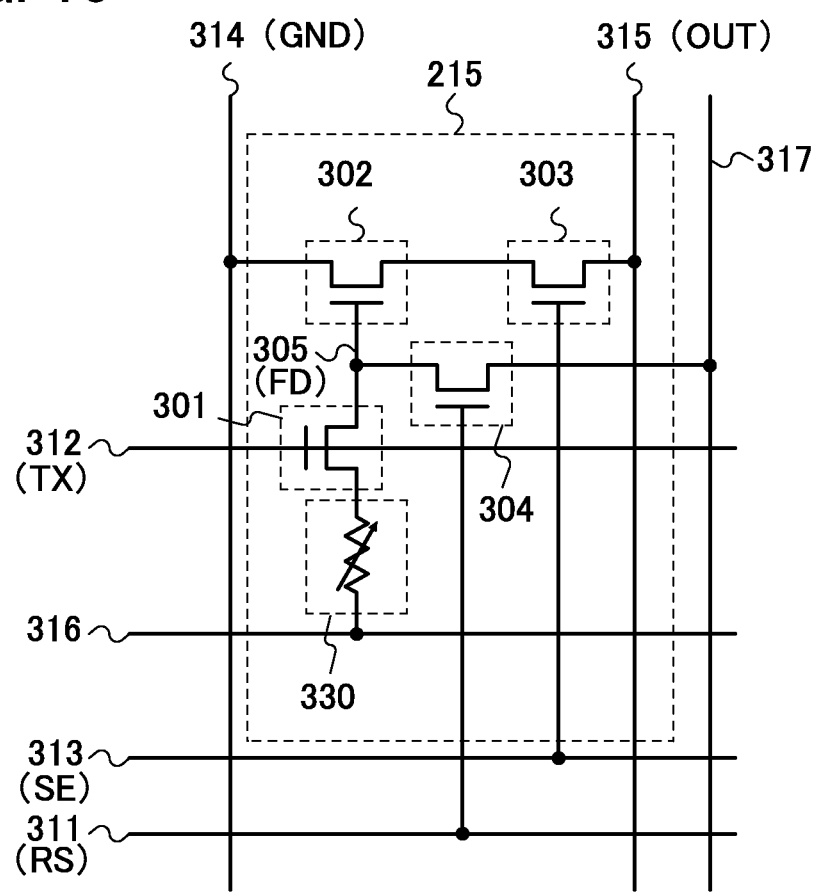
FIG. 10 illustrates a configuration of a pixel circuit.

The pixel circuit 210 may have a configuration illustrated in FIG. 10. A circuit 215 in FIG. 10 has the same configuration as that in FIG. 7A or 7B except that instead of the photodiode, a variable resistor 330 is used as a light-receiving element. The variable resistor can be constituted by a pair of electrodes and an i-type semiconductor layer provided therebetween.

For example, the resistance changes due to visible light irradiation when an i-type amorphous silicon layer is used as the semiconductor layer; thus, the potential of the wiring 305 can be changed as in the case of using the photodiode, which makes it possible to find the amount of light emitted to the variable resistor 330 during the accumulation operation. As the i-type semiconductor layer, an oxide semiconductor layer having a band gap of 3 eV or more may be used. Since the resistance of the oxide semiconductor layer changes due to ultraviolet light irradiation, the potential of the wiring 305 can be changed, which makes it possible to find the amount of light emitted to the variable resistor 330 during the accumulation operation. The type of the scintillator 120 may be changed to select the wavelength of the light emitted to the variable resistor 330.

By setting the potential of the sixth wiring 316 low and the potential of the seventh wiring 317 high, the circuit 215 in FIG. 10 can operate in accordance with the timing chart in FIG. 8A. By setting the potential of the sixth wiring 316 high and the potential of the seventh wiring 317 low, the circuit 215 can operate in accordance with the timing chart in FIG. 8C.

Figure 11A:
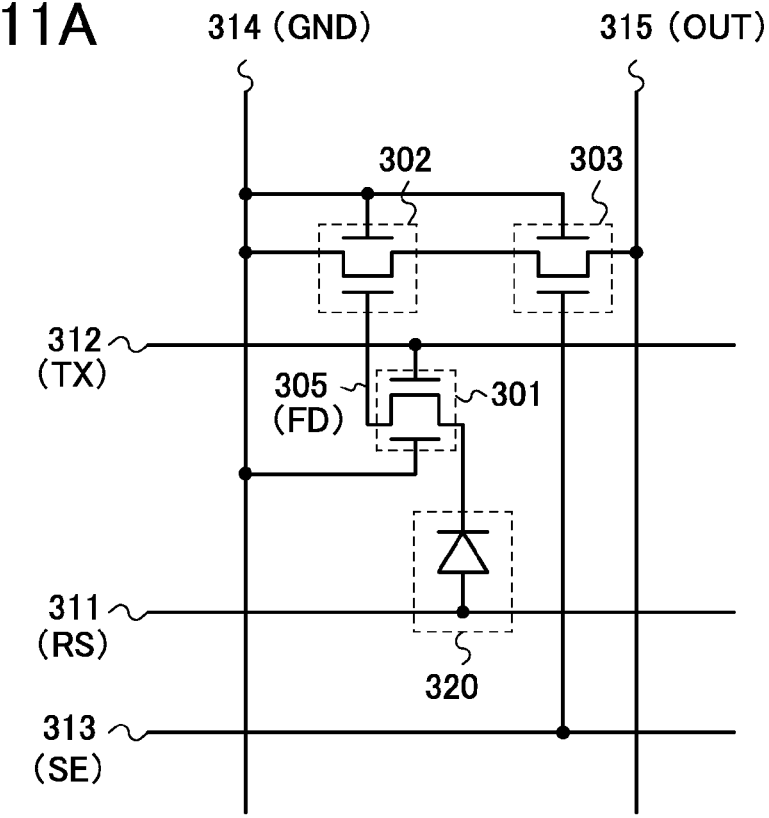
FIGS. 11A and 11B each illustrate a configuration of a pixel circuit.
Figure 11B:
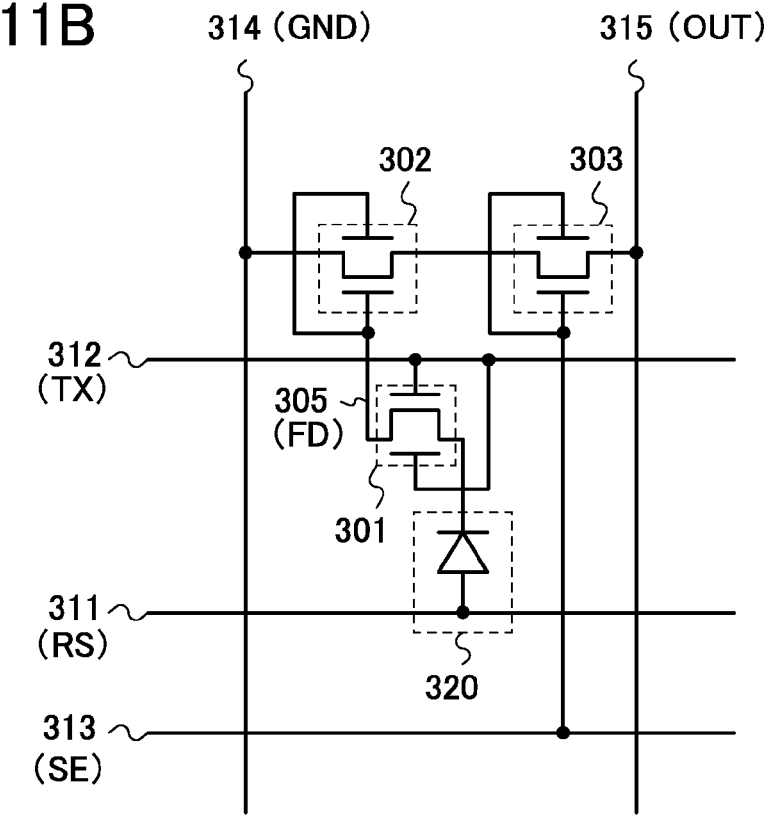

The first transistor 301, the second transistor 302, and the third transistor 303 in the pixel circuit 210 may have back gates as illustrated in FIGS. 11A and 11B. FIG. 11B illustrates a configuration in which the same potential is applied to the front gate and the back gate, which enables an increase in on-state current. FIG. 11A illustrates a configuration in which a constant potential is applied to the back gates, which enables control of the threshold voltage. Although the back gates are electrically connected to the fourth wiring 314 (GND) in the configuration of FIG. 11A, they may be electrically connected to another wiring to which a constant potential is supplied. Note that FIGS. 11A and 11B show an example in which back gates are provided in the transistors of the circuit 211. The circuits 212, 213, 214, 215, 216, and 217 may have the same configuration. Moreover, the configuration of applying the same potential to a front gate and a back gate, the configuration of applying a constant potential to a back gate, and the configuration without a back gate may be used in combination for the transistors in one pixel circuit as necessary.

Figure 12A:
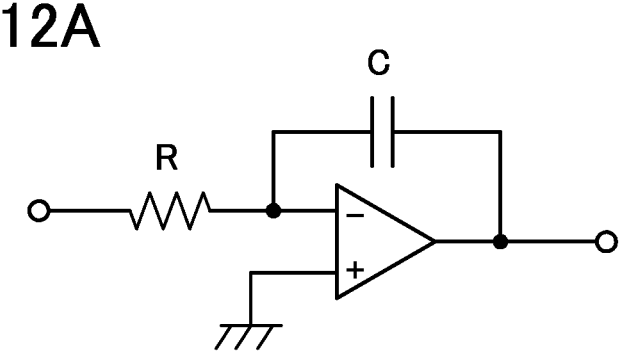
FIGS. 12A to 12C each illustrate an integrator circuit.
Figure 12B:
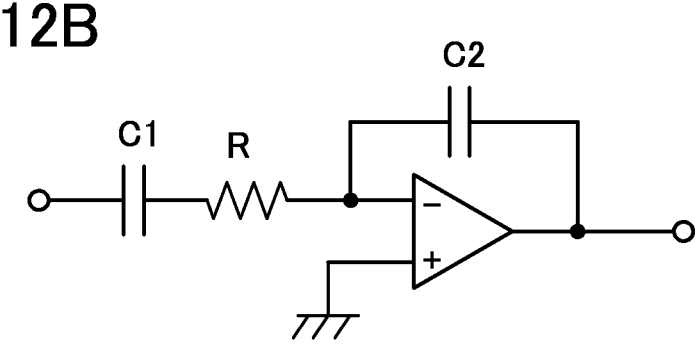
Figure 12C:
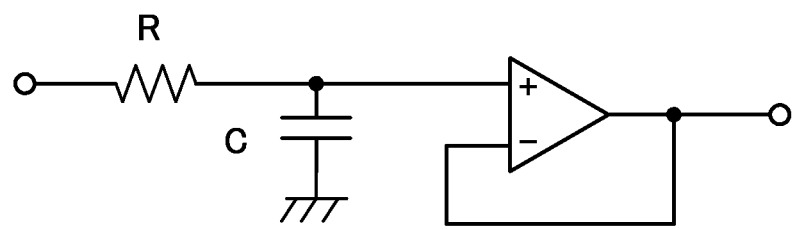

Note that in the above circuit examples, an integrator circuit illustrated in FIG. 12A, 12B, or 12C may be connected to the fifth wiring 315 (OUT). In such a circuit, an S/N ratio of a reading signal can be increased to sense weaker light, that is, the sensitivity of the imaging device can be increased.

FIG. 12A illustrates an integrator circuit using an operational amplifier circuit (also referred to as an op-amp). An inverting input terminal of the operational amplifier circuit is connected to the fifth wiring 315 (OUT) through a resistor R. A non-inverting input terminal of the operational amplifier circuit is grounded. An output terminal of the operational amplifier circuit is connected to the inverting input terminal of the operational amplifier circuit through a capacitor C.

FIG. 12B illustrates an integrator circuit including an operational amplifier circuit having a structure different from that in FIG. 12A. An inverting input terminal of the operational amplifier circuit is connected to the fifth wiring 315 (OUT) through a resistor R and a capacitor Cl. A non-inverting input terminal of the operational amplifier circuit is grounded. An output terminal of the operational amplifier circuit is connected to the inverting input terminal of the operational amplifier circuit through a capacitor C2.

FIG. 12C illustrates an integrator circuit using an operational amplifier circuit having a structure different from those in FIGS. 12A and 12B. A non-inverting input terminal of the operational amplifier circuit is connected to the fifth wiring 315 (OUT) through a resistor R. A non-inverting input terminal of the operational amplifier circuit is connected to an output terminal of the operational amplifier circuit. The resistor R and the capacitor C constitute a CR integrator circuit. The operational amplifier circuit is a unity gain buffer.

This embodiment can be implemented in an appropriate combination with any of the structures described in the other embodiments.

(Embodiment 3)

In this embodiment, an example of the imaging device using radiation such as X-rays, which is different from that shown in Embodiment 1, will be described with reference to drawings. Note that components similar to those in Embodiment 1 are denoted by the same reference numerals and are not described in detail.

Figure 13A:
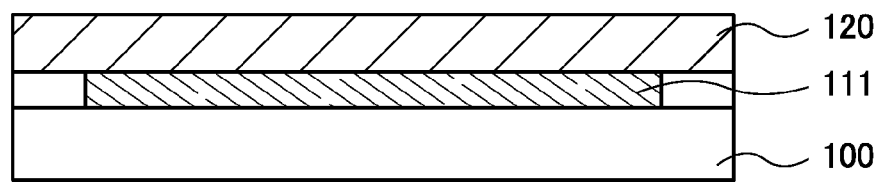
FIGS. 13A to 13C are a cross-sectional view and top views illustrating an imaging device.
Figure 13B:
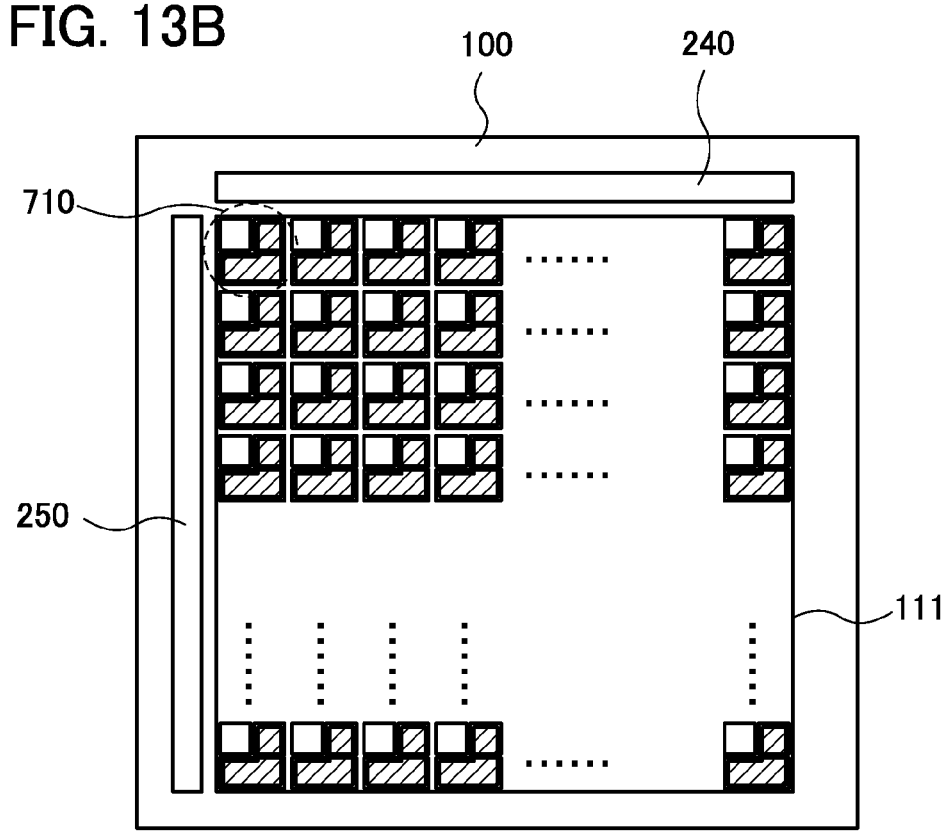

FIGS. 13A and 13B are cross-sectional views each illustrating a structure of the imaging device of one embodiment of the present invention. An imaging device 30 illustrated in FIG. 13A includes a pixel array 111 over the substrate 100, and the scintillator 120 over the pixel array 111.

The pixel array 111 over the substrate 100 can have a structure illustrated in the top view of FIG. 13B, for example. Note that in FIG. 13B, the scintillator 120 is omitted for clarity.

Figure 13C:
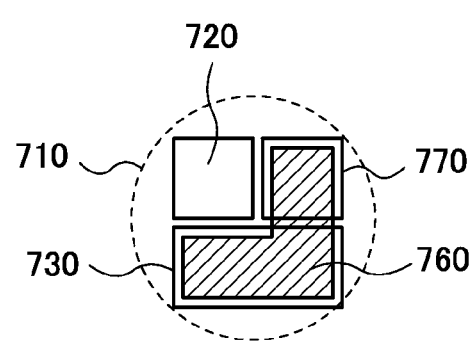

The pixel array 111 includes a plurality of pixel circuits 710 arranged in a matrix, and the pixel circuits 710 each include a light-receiving element 720 and an imaging circuit portion 730 electrically connected to the light-receiving element 720, and a light-emitting element 760 and a light-emitting circuit portion 770 electrically connected to the light-emitting element 760 (see FIG. 13C).

In the imaging device of one embodiment of the present invention, a transistor including an oxide semiconductor in an active layer can be used for the imaging circuit portion 730 and the light-emitting circuit portion 770. The transistor using an oxide semiconductor has a higher mobility than a transistor using amorphous silicon, and is thus easily reduced in size, resulting in a reduction in the size of a pixel. In other words, the resolution of the imaging device can be increased.

As described in Embodiment 1, the transistor including an oxide semiconductor in the active layer is damaged by part of X-rays passing through the scintillator 120. The degradation is recovered by heat treatment using the heater 101 and light irradiation using the light-emitting device 130 in Embodiment 1. In the imaging device 30 of this embodiment, light irradiation using the light-emitting element 760 is performed in addition to the heat treatment using the heater 101.

As the light-emitting element 760, for example, an organic EL element can be used. The light-emitting element preferably emits light with a wavelength of 500 nm to 600 nm, more preferably, approximately 550 nm as described in Embodiment 1.

The light-emitting element 760 is formed over the imaging circuit portion 730 and the light-emitting circuit portion 770 as illustrated in the drawing. Therefore, the light-emitting element 760 preferably has a bottom-emission structure (in which light is emitted to the substrate 100 side) so that both the circuit portions are irradiated with light. In addition, transistors included in the imaging circuit portion 730 and the light-emitting circuit portion 770 preferably have a bottom-gate structure so that active layers of the transistors are irradiated with light effectively.

Figure 14:
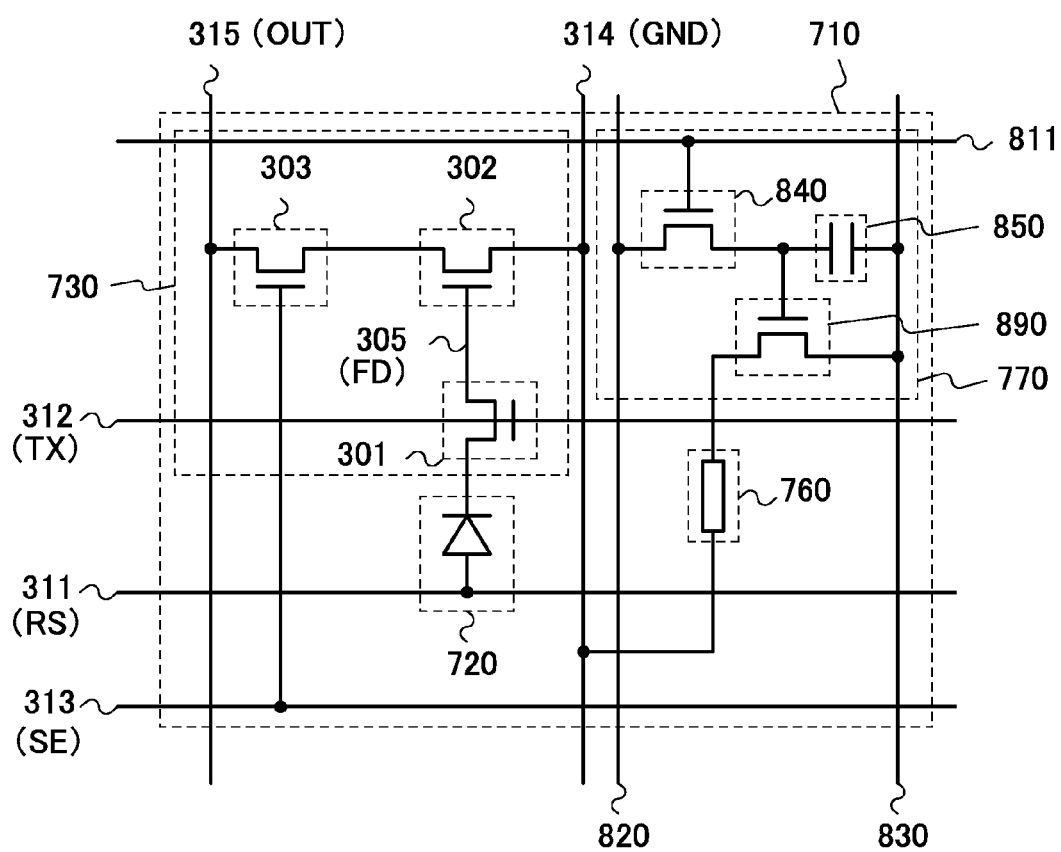
FIG. 14 illustrates a configuration of a pixel circuit.

FIG. 14 is a circuit diagram of the pixel circuit 710 in which the circuit 211 illustrated in FIG. 7A is used as the imaging circuit portion 730 and the light-emitting element 760 and the light-emitting circuit portion 770 are connected with the fourth wiring 314 (GND), a reference potential line, used in common.

In the light-emitting circuit portion 770, one of a source and a drain of a fifth transistor 840 is connected to a signal line 820, the other of the source and the drain of the fifth transistor 840 is connected to a gate of a sixth transistor 890 and one electrode of a capacitor 850, a gate of the fifth transistor 840 is connected to a scanning line 811, one of a source and a drain of the sixth transistor 890 is connected to a power source line 830, the other of the source and the drain of the sixth transistor 890 is connected to one electrode of the light-emitting element 760, and the other electrode of the light-emitting element 760 is connected to the fourth wiring 314 (GND).

Light emission can be maintained in the light-emitting element 760 and the light-emitting circuit portion 770 in the following manner by utilizing the feature that the potential of at least the capacitor 850 can be retained.

First, a potential that turns the fifth transistor 840 on is supplied to the scanning line 811. As a result, the potential of the signal line 820 is supplied to the one electrode of the capacitor 850 and the gate electrode of the sixth transistor 890. That is, a predetermined charge is applied to a node including the capacitor 850 and the gate of the sixth transistor 890. The sixth transistor 890 makes a current corresponding to the potential of the node flow into the light-emitting element 760, thereby controlling the emission intensity.

After that, the fifth transistor 840 is turned off when a potential that turns the fifth transistor 840 off is supplied to the scanning line 811. Thus, the potential of the node including the capacitor 850 and the gate of the sixth transistor 890 is retained, so that emission from the light-emitting element 760 is maintained. Note that the potential of the node can be retained for a long time if a transistor using an oxide semiconductor and having an extremely low off-state current is used as the fifth transistor 840. Hence, the emission intensity of the light-emitting element 760 can be maintained for a long period even when the interval between operations for supplying a potential to the node increases, leading to a reduced power consumption.

Light from the light-emitting element is emitted to the active layers of the transistors included in the imaging circuit portion 730 and the light-emitting circuit portion 770; thus, degradation of the electrical characteristics due to X-ray irradiation can be recovered.

Figure 15:
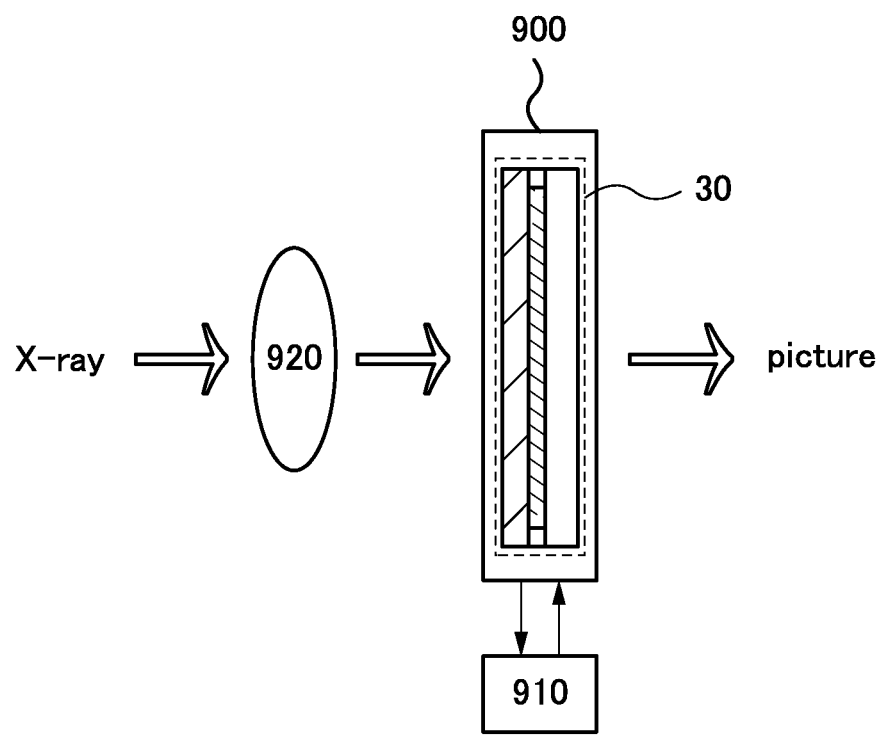
FIG. 15 illustrates an imaging device having a display function.

Note that the imaging device 30 can be used as a display device if openings are provided in the imaging circuit portion 730 and the light-emitting circuit portion 770 and the substrate 100 and the heater 101 are made of a material that transmits light emitted from the light-emitting element 760. For example, as illustrated in FIG. 15, X-rays passing through a subject 920 enters the input side (the scintillator 120 side) of an imaging system 900 including the imaging device 30. Then, an image signal output from the imaging circuit portion 730 in the imaging device 30 is converted into a grayscale signal by a signal processing device 910 and input to the light-emitting circuit portion 770 in the imaging device 30. As a result, an image can be displayed on the output side (the substrate 100 side) of the imaging system 900.

This embodiment can be implemented in an appropriate combination with any of the structures described in the other embodiments.

(Embodiment 4)

In this embodiment, an example of a driving method of the pixel circuit shown in Embodiment 2 will be described.

As described in Embodiment 2, the operation of the pixel circuit is repetition of the reset operation, the accumulation operation, and the selection operation. In the imaging device using radiation such as X-rays, radiation time is preferably as short as possible in consideration of influence on the living body. To shorten the radiation time and perform imaging in a short time, the reset operation, the accumulation operation, and the selection operation need to be carried out at high speed in all the pixel circuits.

Figure 16A:
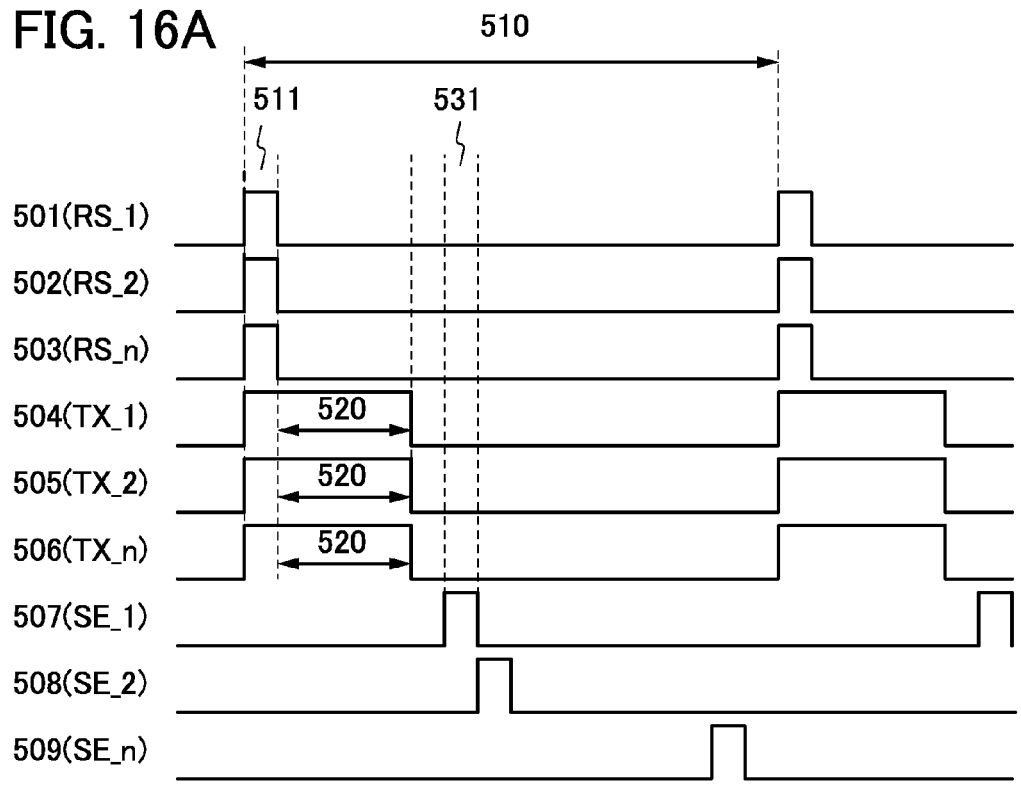
FIGS. 16A and 16B are timing charts showing the operations in a global shutter system and a rolling shutter system, respectively.

Thus, a driving method using a global shutter system shown in the timing chart in FIG. 16A is preferably used for imaging. FIG. 16A shows operations of an imaging device in which a plurality of pixel circuits 211 illustrated in FIG. 7A are arranged in a matrix. Specifically, FIG. 16A show operations of the circuits 211 from the first row to the n-th row (n is a natural number of three or more). The operation described below can be applied to the circuit 213 in FIG. 9A, the circuit 215 in FIG. 10, and the circuits in FIGS. 11A and 11B.

In FIG. 16A, a signal 501, a signal 502, and a signal 503 are input to the first wirings 311 (RS) connected to the pixel circuits in the first row, the second row, and the n-th row, respectively. A signal 504, a signal 505, and a signal 506 are input to the second wirings 312 (TX) connected to the pixel circuits in the first row, the second row, and the n-th row, respectively. A signal 507, a signal 508, and a signal 509 are input to the third wirings 313 (SE) connected to the pixel circuits in the first row, the second row, and the n-th row, respectively.

A period 510 is the time taken for one imaging. In a period 511, the pixel circuits in each row perform the reset operation at the same time. In a period 520, the pixel circuits in each row perform the accumulation operation at the same time. The selection operation of the pixel circuits is sequentially performed on the row basis. For example, the selection operation is performed in the pixel circuits in the first row in a period 531. In this manner, in the global shutter system, the reset operation is performed in all the pixel circuits substantially at the same time, the accumulation operation is performed in all the pixel circuits substantially at the same time, and then the read operation is sequentially performed on the row basis.

That is, in the global shutter system, the accumulation operation is performed in all the pixel circuits substantially at the same time; accordingly, imaging is simultaneously performed in the pixel circuits in all the rows. Radiation is thus in synchronization with the accumulation operation, leading to a reduction in radiation time. That is, in the global shutter system, radiation needs to be performed only in the period 520.

Figure 16B:
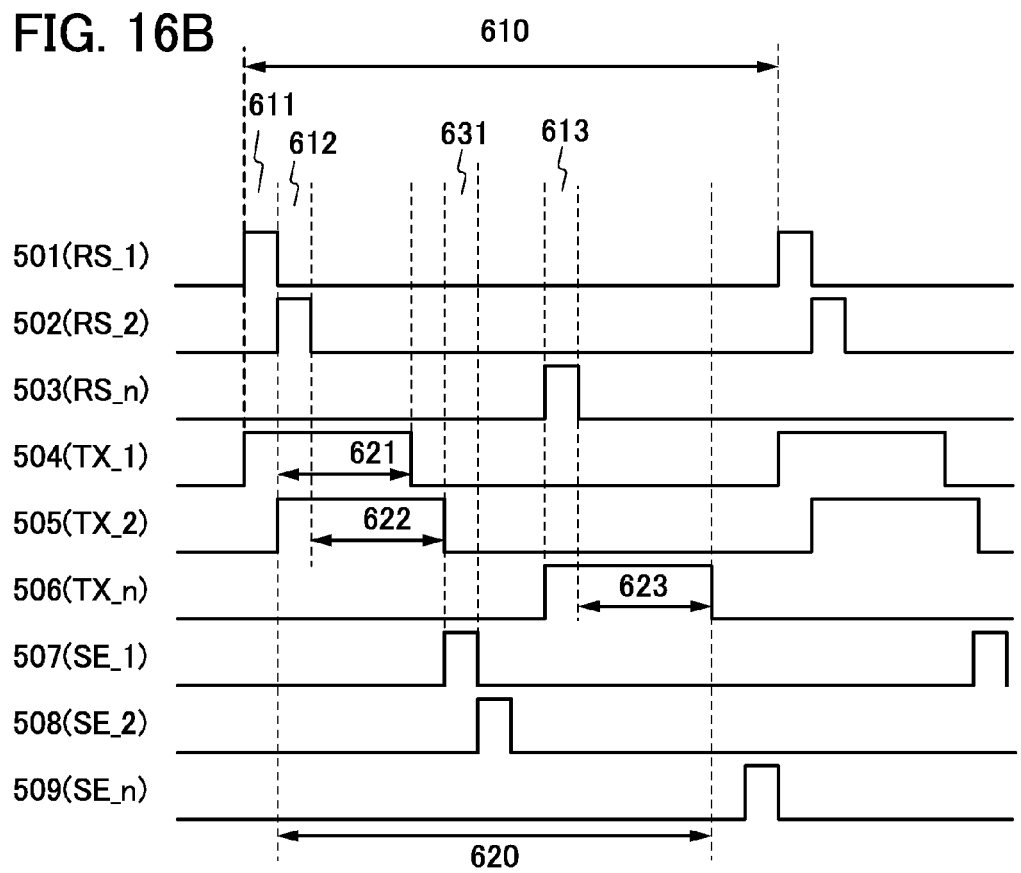

FIG. 16B is a timing chart of operation using a rolling shutter system. The description of FIG. 16A can be referred to for the signals 501 to 509. A period 610 is the time taken for one imaging. A period 611, a period 612, and a period 613 are reset periods in the first row, the second row, and the n-th row, respectively. A period 621, a period 622, and a period 623 are accumulation operation periods in the first row, the second row, and the n-th row, respectively. In a period 631, the selection operation is performed in the pixel circuits in the first row. Thus, in the rolling shutter system, the accumulation operation is not performed at the same time in all the pixel circuits but is sequentially performed on the row basis; accordingly, imaging is not simultaneously performed in the pixel circuits in all the rows. For this reason, even when the radiation is synchronized with the accumulation operation, a radiation period 620 (the sum of the periods 621 to 623) is longer than the period 520 in the global shutter system. However, the radiation period 620 can be shortened, for example, by reducing the accumulation operation period; thus, the rolling shutter system can also be used as a driving method of the imaging device of one embodiment of the present invention.

To perform the global shutter system, even after the accumulation operation, the potential of the wiring 305 (FD) in each pixel circuit needs to be kept for a long time until the read operation is performed. As described above, when a transistor including a channel formation region formed of an oxide semiconductor, which has an extremely low off-state current, is used as the first transistor 301, the potential of the wiring 305 (FD) can be kept for a long time. In the case where a transistor including a channel formation region formed of a silicon semiconductor or the like is used as the first transistor 301, the potential of the wiring 305 (FD) cannot be kept for a long time because of a high off-state current, which makes it difficult to use the global shutter system.

The use of transistors including a channel formation region formed of an oxide semiconductor in the pixel circuits makes it easy to perform the global shutter system; accordingly, the imaging device that allows for a low dose of radiation emitted to a subject can be provided.

This embodiment can be implemented in an appropriate combination with any of the structures described in the other embodiments.

This application is based on Japanese Patent Application serial No. 2013-179560 filed with Japan Patent Office on Aug. 30, 2013, the entire contents of which are hereby incorporated by reference.

What is claimed is:

1. An imaging device comprising:
a substrate provided with a heater;
a pixel array on the substrate, the pixel array including a plurality of pixel circuits, each pixel circuit comprising a light-receiving element, an imaging circuit portion electrically connected to the light-receiving element, a light-emitting element, and a light-emitting circuit portion electrically connected to the light-emitting element; and
a scintillator on the pixel array.

2. The imaging device according to claim 1, wherein the pixel circuit includes a transistor comprising an oxide semiconductor in a channel formation region.

3. The imaging device according to claim 2, wherein the oxide semiconductor comprises indium, gallium, and zinc.

4. The imaging device according to claim 1, wherein the light-receiving element is a photodiode.

5. The imaging device according to claim 1, wherein the light-receiving element is a variable resistor including a semiconductor layer between a pair of electrodes.

6. The imaging device according to claim 1, wherein the heater comprises a material selected from the group consisting of tungsten, chromium, titanium, titanium nitride, tantalum nitride, zinc oxide, tin oxide, and indium oxide.

7. The imaging device according to claim 1, wherein the substrate has light-transmitting properties.

8. The imaging device according to claim 1, wherein the light-emitting element is configured to emit light to the imaging circuit portion and the light-emitting circuit portion.

9. An imaging device comprising:
a light-emitting device;
a substrate on the light-emitting device, the substrate being provided with a heater;
a pixel array on the substrate, the pixel array including a plurality of pixel circuits, each pixel circuit comprising a light-receiving element and a circuit portion electrically connected to the light-receiving element; and
a scintillator on the pixel array,
wherein the circuit portion includes a transistor, and
wherein the light-emitting device is configured to emit light to the transistor in the circuit portion through the substrate.

10. The imaging device according to claim 9, wherein the light emitted from the light-emitting device is monochromatic light with a wavelength range from 500 nm to 600 nm or a mixture of colors including light in the wavelength range.

11. The imaging device according to claim 9, wherein the transistor comprises an oxide semiconductor in a channel formation region.

12. The imaging device according to claim 11, wherein the oxide semiconductor comprises indium, gallium, and zinc.

13. The imaging device according to claim 9, wherein the light-receiving element is a photodiode.

14. The imaging device according to claim 9, wherein the light-receiving element is a variable resistor including a semiconductor layer between a pair of electrodes.

15. The imaging device according to claim 9, wherein the heater comprises a material selected from the group consisting of tungsten, chromium, titanium, titanium nitride, tantalum nitride, zinc oxide, tin oxide, and indium oxide.

16. The imaging device according to claim 9, wherein the substrate has light-transmitting properties.

17. An imaging device comprising:
a substrate provided with a heater;
a pixel array on the substrate, the pixel array including a plurality of pixel circuits, each pixel circuit comprising a light-receiving element, an imaging circuit portion electrically connected to the light-receiving element, a light-emitting element, and a light-emitting circuit portion electrically connected to the light-emitting element, wherein the light-emitting element is provided over the imaging circuit portion and the light-emitting circuit portion; and
a scintillator on the pixel array.

18. The imaging device according to claim 17, wherein the light-receiving element is a photodiode.

19. The imaging device according to claim 17, wherein the light-receiving element is a variable resistor including a semiconductor layer between a pair of electrodes.

20. The imaging device according to claim 17, wherein the heater comprises a material selected from the group consisting of tungsten, chromium, titanium, titanium nitride, tantalum nitride, zinc oxide, tin oxide, and indium oxide.

21. The imaging device according to claim 17, wherein the substrate has light-transmitting properties.

22. The imaging device according to claim 17, wherein the light-emitting element emits monochromatic light with a wavelength range from 500 nm to 600 nm or a mixture of colors including light in the wavelength range.

23. The imaging device according to claim 17, wherein the pixel circuit includes a transistor comprising an oxide semiconductor in a channel formation region.

24. The imaging device according to claim 23, wherein the oxide semiconductor comprises indium, gallium, and zinc.

25. The imaging device according to claim 17, wherein the light-emitting element is configured to emit light to the imaging circuit portion and the light-emitting circuit portion.

* * * * *